United States Patent [19]

Kunz et al.

[11] Patent Number: 4,663,463
[45] Date of Patent: May 5, 1987

[54] MANDELIC ACID DERIVATIVES AND MANDELONITRILES, PROCESSES FOR PRODUCING THEM, AND THEIR USE FOR COMBATING MICROORGANISMS

[75] Inventors: Walter Kunz, Oberwil, Switzerland; Wolfgang Eckhardt, Lörrach, Fed. Rep. of Germany

[73] Assignee: Ciba-Geigy Corporation, Ardsley, N.Y.

[21] Appl. No.: 676,765

[22] Filed: Nov. 30, 1984

Related U.S. Application Data

[62] Division of Ser. No. 383,398, Jun. 1, 1982, abandoned.

[30] Foreign Application Priority Data

Jun. 4, 1981 [CH] Switzerland ............ 3674/81
May 7, 1982 [CH] Switzerland ............ 2840/82

[51] Int. Cl.[4] ............... C07D 249/10; C07D 233/64
[52] U.S. Cl. ..................... 548/262; 548/336; 548/341; 546/276
[58] Field of Search ............ 546/276; 548/262, 336, 548/341

[56] References Cited

U.S. PATENT DOCUMENTS

| | | | |
|---|---|---|---|
| 4,331,674 | 5/1982 | Kramer et al. | 544/366 |
| 4,366,152 | 12/1982 | Kramer et al. | 548/262 |
| 4,366,165 | 12/1982 | Miller et al. | 548/101 |
| 4,414,210 | 11/1983 | Miller et al. | 548/101 |

FOREIGN PATENT DOCUMENTS 2640823 3/1977 Fed. Rep. of Germany ...... 548/262
2908323 9/1980 Fed. Rep. of Germany ...... 514/383

Primary Examiner—Glennon H. Hollrah
Assistant Examiner—D. L. Dinner
Attorney, Agent, or Firm—Edward McC. Roberts; Meredith C. Findlay

[57] ABSTRACT

There are described microbicidally effective mandelic acid derivatives and mandelonitriles of the formula I

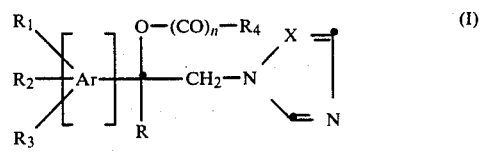

wherein X is —CH= or —N=; Ar is phenyl, diphenyl or naphthyl group, which can be substituted in the form of the substituents $R_1$-$R_3$ by nitro, halogen, alkyl, alkoxy or haloalkyl; R is any one of the groups —COOR$_5$, —COSR$_6$, —CON(R$_7$)(R$_8$) or CN; n is 0, 1 or 2; and $R_4$ to $R_8$ are aliphatic and aromatic and in part also heterocyclic substituents which are described in the text in greater detail; with the inclusion of the salts and metal complexes thereof.

Also methods for producing these products are disclosed, and also pesticidal compositions containing as active ingredient one of these compounds. There is described too a method for combating phytopathogenic microorganisms with the aid of these substances.

1 Claim, No Drawings

MANDELIC ACID DERIVATIVES AND MANDELONITRILES, PROCESSES FOR PRODUCING THEM, AND THEIR USE FOR COMBATING MICROORGANISMS

This is a division of application Ser. No. 383,398 filed on June 1, 1982 now abandoned.

The present invention relates to mandelic acid derivatives and mandelonitriles of the following formula I, and also to their acid addition salts, quaternary azolium salts and metal complexes which have tolerance to plants. It relates also to the production of these compounds, as well as to agrochemical compositions which contain as active ingredients at least one of the compounds of the formula I; it relates also to the production of the compositions, and to a process for combating or preventing an infestation of plants by microorganisms.

The compounds according to the invention correspond to the formula I

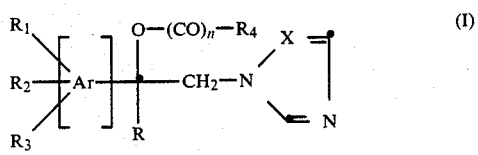  (I)

wherein

X is the bridge member —CH= or —N=;
Ar is a phenyl, diphenyl or naphthyl group;
$R_1$, $R_2$ and $R_3$ independently of one another are each hydrogen, nitro, halogen, $C_1$–$C_3$-alkyl, $C_1$–$C_3$-alkoxy or $C_1$–$C_3$-haloalkyl;
R is one of the groups —COOR$_5$, —COSR$_6$,

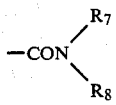

or —CN;
n is the number 0, 1 or 2, where in the cases in which n is the number 0
$R_4$ is hydrogen, $C_1$–$C_{12}$-alkyl, $C_3$–$C_6$-alkenyl, $C_3$–$C_6$-haloalkenyl, or $C_1$–$C_{12}$-alkyl substituted by $C_1$–$C_4$-alkoxy, $C_2$–$C_4$-alkenyl, $C_2$–$C_4$-haloalkenyl, $C_2$–$C_4$-alkynyl, cyano or phenyl, or $C_2$–$C_{12}$-alkyl interrupted by a carbonyl group or a carbamoyloxy group (—O—CONH—), in the cases in which n is 1
$R_4$ is $C_1$–$C_{12}$-alkyl, phenyl, $C_1$–$C_4$-alkoxy, $C_1$–$C_4$-alkylthio, $C_2$–$C_6$-alkenyl, $C_3$–$C_5$-alkynyl, $C_2$–$C_6$-haloalkenyl, $C_3$–$C_7$-cycloalkyl, furyl, tetrahydrofuryl, pyridyl, 1-imidazolyl or 1-(1,2,4-triazolyl), or a phenyl group which is unsubstituted or substituted by halogen, $C_1$–$C_4$-alkyl, $C_1$–$C_4$-alkoxy, —CN or —CF$_3$, or a $C_1$–$C_{12}$-alkyl group substituted by $C_1$–$C_4$-alkoxy, $C_1$–$C_4$-alkylthio, $C_2$–$C_4$-alkenyl, $C_2$–$C_4$-haloalkenyl, $C_2$–$C_4$-alkynyl, cyano or phenyl, each heterocyclic substituent being unsubstituted or mono- or polysubstituted by halogen and/or methyl, and each $C_2$–$C_{12}$-alkyl substituent being able to be interrupted by a carbonyl group or a carbamoyloxy group, and $R_4$ can also be the group —N($C_1$–$C_8$-alkyl)$_2$, and in the cases in which n is 2
$R_4$ is $C_1$–$C_{12}$-alkyl, or a benzyl group which is unsubstituted or substituted by halogen, $C_1$–$C_4$-alkyl, $C_1$–$C_4$-alkoxy, —CN or CF$_3$;
$R_5$ is hydrogen, a $C_2$–$C_{10}$-alkenyl group which is unsubstituted or substituted by halogen, a $C_2$–$C_{10}$-alkynyl group which is unsubstituted or substituted by halogen, or it is a $C_3$–$C_8$-cycloalkyl group, or a phenyl group which is unsubstituted or substituted by halogen, $C_1$–$C_4$-alkyl, $C_1$–$C_4$-alkoxy, —CN or —CF$_3$, or it is a $C_1$–$C_{12}$-alkyl chain, which from $C_2$-alkyl can be interrupted by oxygen or sulfur, and which can be unsubstituted or substituted by one of the following atoms or groups: halogen, phenyl, —COO-alkyl($C_1$–$C_4$), —CO-alkyl($C_1$–$C_4$), —CO-phenyl, or an unsaturated or saturated 5- or 6-membered ring with oxygen or sulfur as hetero atom;
$R_6$ is $C_1$–$C_{10}$-alkyl, or a phenyl or benzyl group each unsubstituted or substituted by halogen, $C_1$–$C_4$-alkyl, $C_1$–$C_4$-alkoxy, —CN or —CF$_3$;
$R_7$ and $R_8$ independently of one another are each hydrogen, $C_1$–$C_6$-alkyl, $C_3$–$C_7$-cycloalkyl or a phenyl or benzyl group, where in each case the aromatic ring is unsubstituted or substituted by halogen, $C_1$–$C_4$-alkyl, $C_1$–$C_4$-alkoxy, —CN or —CF$_3$, or where one of the substituents $R_7$ or $R_8$ is also the group —N($R_9$)($R_{10}$), or where the substituents $R_7$ and $R_8$ together form a 5- or 6-membered, saturated or unsaturated, heterocyclic ring, which can contain 1 or 2 further N atoms; and
$R_9$ and $R_{10}$ independently of one another are each hydrogen or $C_1$–$C_4$-alkyl, or a phenyl group which is unsubstituted or substituted by halogen, $C_1$–$C_4$-alkyl, —CN or —CF$_3$;

and wherein acid addition salts, quaternary azolium and ammonium salts, as well as metal complexes of the formula I, are included.

By alkyl or by alkyl moiety of another substituent are meant, depending on the given number of carbon atoms, for example the following groups: methyl, ethyl, propyl, butyl, pentyl, hexyl, heptyl, octyl, nonyl, decyl, undecyl or dodecyl, as well as isomers thereof, such as isopropyl, isobutyl, tert-butyl, isopentyl, and so forth. Alkenyl is for example vinyl, propenyl-(1), allyl, butenyl-(1), butenyl-(2), butenyl-(3), and so forth, as well as chains having several double bonds. Alkynyl is for example propynyl-(1), propargyl, butynyl-(1), butynyl-(2), and so forth, preferably propargyl. Haloalkyl is a mono- to perhalogenated alkyl substituent, such as CHCl$_2$, CH$_2$Cl, CCl$_3$, CF$_3$, CH$_2$CH$_2$Cl, and so forth. The term 'halogen' denotes, here and in the following: fluorine, chlorine, bromine or iodine, preferably chlorine or fluorine. Cycloalkyl is for example: cyclopropyl, cyclobutyl, cyclopentyl cyclohexyl or cycloheptyl, preferably cyclopropyl and cyclohexyl. Haloalkenyl is an alkenyl group which is mono- or polysubstituted by halogen, chlorine and bromine, particularly chlorine, being preferred as halogen. Furyl is preferably 2-furyl; tetrahydrofuryl is preferably 2-tetrahydrofuryl, and pyridyl is in particular 3- or 4-pyridyl. Naphthyl is α- or β-naphthyl, especially α-naphthyl. Examples of heterocyclic 5-or 6-membered rings having up to 3N atoms are pyrazole, imidazole, 1,2,4-triazole and 1,3,4-triazole, pyridine, pyrazine, pyrimidine, pyridazine, 1,3,5-triazine and 1,2,4-triazine.

Examples of salt-forming acids are inorganic acids: hydrohalic acid, such as hydrofluoric acid, hydrochloric acid, hydrobromic acid or hydriodic acid, as well as sulfuric acid, phosphoric acid, phosphorous acid or nitric acid, and organic acids, such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid or 2-acetoxybenzoic acid.

Metal complexes of the formula I consist of the basic organic molcule and an inorganic or organic metal salt, for example the halides, nitrates, sulfates, phosphates, acetates, trifluoroacetates, trichloroacetates, propionates, tartrates, sulfonates, salicylates, benzoates, and the like, of the elements of the third and fourth main group, such as aluminium, tin or lead, and also of the first to the eighth subgroup, such as chromium, manganese, iron, cobalt, nickel, copper, zinc, silver, mercury, and so forth. The subgroup elements of the 4th period are preferred. The metals can be present here in the various valencies in which they occur. The metal complexes of the formula I can be mononuclear or polynuclear in form, that is to say, they can contain one or more organic molecule constituents as ligands. Complexes with the metals copper, zinc, manganese and tin are preferred.

The compounds of the formula I are, at room temperature, stable oils, resins or largely solids, which are distinguished by very valuable microbicidal properties. They can be used in agriculture or in related fields in a preventive and curative manner for combating phytopathogenic microorganisms, the preferred compounds being the triazolylmethyl derivatives embraced by the formula I (X is N). The active substances of the formula I according to the invention are characterised by very good tolerance to cultivated plants. The development of the plants is not at any stage impeded or retarded.

A part of the scope of the present invention relates to compounds of the formula I*

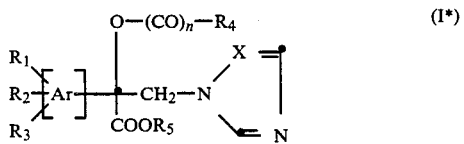

wherein

X is the bridge member —CH= or —N=;

Ar is a phenyl, diphenyl or naphthyl group;

$R_1$, $R_2$ and $R_3$ independently of one another are each hydrogen, nitro, halogen, $C_1$-$C_3$-alkyl, $C_1$-$C_3$-alkoxy or $C_1$-$C_3$-haloalkyl;

n is the number 0 or 1, and in the cases in which n is the number 0

$R_4$ is hydrogen, $C_1$-$C_{12}$-alkyl, $C_3$-$C_6$-alkenyl, $C_3$-$C_6$-haloalkenyl, or $C_1$-$C_{12}$-alkyl substituted by $C_1$-$C_4$-alkoxy, $C_2$-$C_4$-alkenyl, $C_2$-$C_4$-haloalkenyl, $C_2$-$C_4$-alkynyl, cyano or phenyl, or $C_2$-$C_{12}$-alkyl interrupted by a carbonyl group, and in the cases in which n is the number 1

$R_4$ is $C_1$-$C_{12}$-alkyl, phenyl, $C_1$-$C_4$-alkoxy, $C_2$-$C_6$-alkenyl, $C_3$-$C_5$-alkynyl, $C_2$-$C_6$-haloalkenyl, $C_3$-$C_7$-cycloalkyl, furyl, tetrahydrofuryl or pyridyl, or a $C_1$-$C_{12}$-alkyl group substituted by $C_1$-$C_4$-alkoxy, $C_2$-$C_4$-alkenyl, $C_2$-$C_4$-haloalkenyl, $C_2$-$C_4$-alkynyl, cyano or phenyl, each cyclic substituent being unsubstituted or mono- or polysubstituted by halogen and/or methyl, and each $C_2$-$C_{12}$-alkyl substituent being able to be interrupted by a carbonyl group; and $R_5$ is hydrogen, $C_1$-$C_4$-alkyl or phenyl, or a phenyl or benzyl group each mono- or polysubstituted by nitro, halogen and/or methyl;

with the inclusion of the acid addition salts, quaternary azolium salts and metal complexes of the compounds of the formula I* which have tolerance to plants.

An important group of compounds are the mandelic acid derivatives and mandelonitriles of the formula I which are unsubstituted on the hydroxyl group, in which X, Ar, R, $R_1$, $R_2$ and $R_3$ have the meanings defined under the formula I, whilst n is nought and $R_4$ is hydrogen.

Within this last-mentioned group, compounds of special importance are those wherein Ar is a phenyl group, and R is any one of the groups: —$COOR_5$, —$COSR_6$ or —$CON(R_7)(R_8)$, the symbols X, $R_1$, $R_2$, $R_3$ and $R_5$-$R_8$ having the meanings defined under the formula I.

Particularly preferred among the last-named compounds are those wherein Ar is phenyl, $R_1$ is halogen, methyl, methoxy or trifluoromethyl, and $R_2$ and $R_3$ independently of one another are each hydrogen, fluorine, chlorine, bromine, methyl or methoxy, whilst X and $R_5$-$R_8$ have the meanings defined under the formula I.

And preferred compounds amongst these are those wherein $R_5$ is hydrogen, $C_1$-$C_6$-alkyl, a phenyl or benzyl group each unsubstituted or substituted by halogen, $C_1$-$C_4$-alkyl, $C_1$-$C_4$-alkoxy, —CN or —$CF_3$, or it is $C_3$-$C_4$-alkenyl or $C_3$-$C_6$-cycloalkyl; $R_6$ is $C_1$-$C_6$-alkyl or a phenyl or benzyl group; $R_7$ is hydrogen or $C_1$-$C_4$-alkyl; and $R_8$ is hydrogen, $C_1$-$C_4$-alkyl, phenyl or benzyl. This last-mentioned group is to be designated as subgroup T.

A preferred group of microbicidal active substances comprises compounds of the formula I* wherein X is —CH= or —N=; Ar is phenyl; $R_1$, $R_2$ and $R_3$ independently of one another are each halogen, methyl, methoxy or trifluoromethyl; n is the number 0 or 1; and $R_4$ and $R_5$ have the meanings defined under the formula I*.

Particularly preferred within this group are those compounds of the formula I* wherein X is —N=; $R_1$, $R_2$ and $R_3$ independently of one another are each fluorine, chlorine, bromine, methyl, methoxy or trifluoromethyl; n is the number 0; $R_4$ is hydrogen, $C_1$-$C_6$-alkyl, $C_3$-$C_6$-alkenyl or $C_3$-$C_6$-haloalkenyl; and $R_5$ has the meanings defined under the formula I*.

A specially preferred group is formed by those compounds of the formula I* wherein X is —N=; Ar is a phenyl group; two of the substituents $R_1$, $R_2$ and $R_3$ are halogen and/or methyl, and the third is hydrogen; $R_4$ is hydrogen or $C_1$-$C_3$-alkyl; and $R_5$ is $C_1$-$C_3$-alkyl, phenyl or benzyl.

A further preferred group of microbicides consists of compounds of the formula I* wherein X, Ar, $R_1$, $R_2$, $R_3$ and $R_5$ are as defined under the formula I*; $R_4$ is hydrogen or $C_1$-$C_3$-alkyl; and n is the number 0.

A group of microbicides especially preferred is formed by compounds of the formula I* wherein Ar is 2,4-dihalophenyl, 4-halophenyl, 2-($C_1$-$C_2$-alkyl)-4-halophenyl or 2-($CF_3$)-4-halophenyl; n is the number 0 or 1; X is —N=; $R_4$ is hydrogen, $C_1$-$C_4$-alkyl, cyclopropyl, cyclohexyl, $C_2$-$C_3$-alkenyl or $C_2$-$C_3$-haloalkenyl; and $R_5$ is $C_1$-$C_4$-alkyl, 2,4-dihalophenyl, 4-halophenyl or phenyl. Particularly preferred substituents in the phenyl moieties mentioned are: fluorine, chlorine, bromine, methyl, methoxy and trifluoromethyl.

Also preferred are microbicides of the formula I* in which X is —N=; $R_1$, $R_2$ and $R_3$ independently of one another are each fluorine, chlorine, bromine, methyl, methoxy or trifluoromethyl; n is the number 1; $R_4$ is hydrogen, $C_1$–$C_6$-alkyl, phenyl, $C_1$–$C_3$-alkoxy, benzyl, $C_3$–$C_6$-cycloalkyl, 2-furyl, 2-tetrahydrofuryl, 3-pyridyl, 4-pyridyl, 5-chloro-2-furyl or halophenyl; and Ar and $R_5$ have the meanings defined under the formula I*.

Further compounds of the formula I* which are of interest are those wherein n is the number 1; X is —CH= or —N=; Ar is diphenyl; $R_1$, $R_2$ and $R_3$ independently of one another are each halogen, methyl or methoxy; n is the number 0 or 1; $R_4$ is hydrogen, $C_1$–$C_3$-alkyl, phenyl, $C_1$–$C_3$-alkoxy, $C_3$–$C_6$-cycloalkyl or furyl; and $R_5$ is hydrogen, $C_1$–$C_3$-alkyl, phenyl or halophenyl.

The following individual substances are particularly preferred as microbicides:

2-(1H-1,2,4-triazolylmethyl-1'-yl)-2-hydroxy-2,4-dichlorophenylacetic acid methyl ester (compound No. 1.1), 2-(1H-1,2,4-triazolylmethyl-1'-yl)-2-hydroxy-2,4-dichlorophenylacetic acid ethyl ester (compound No. 1.9), 2-(1H-1,2,4-triazolylmethyl-1'-yl)-2-hydroxy-2,4-dichlorophenylacetic acid-n-propyl ester (compound No. 1.10), 2-(1H-1,2,4-triazolylmethyl-1'-yl)-2-hydroxy-2,4-dichlorophenylacetic acid-n-butyl ester (compound No. 1.14), 2-(1H-1,2,4-triazolylmethyl-1'-yl)-2-ethylthiocarbonyloxy-2-(2'-chloro-4'-fluorophenyl)-acetic acid ethyl ester (compound No. 2.161), 2-(1H-1,2,4-triazolylmethyl-1'-yl)-2-hydroxy-2-chloro-4-bromophenylacetic acid methyl ester (compound No. 1.27), 2-(1H-1,2,4-triazolylmethyl-1'-yl)-2-hydroxy-2-chloro-4-bromophenylacetic acid ethyl ester (compound No. 1.29), 2-(1H-1,2,4-triazolylmethyl-1'-yl)-2-ethoxy-2,4-dichlorophenylacetic acid ethyl ester (compound No. 3.3), 2-(1H-1,2,4-triazolylmethyl-1'-yl)-2-hydroxy-2,4-dichlorophenylacetic acid tert-butyl ester (compound No. 1.24), 2-(1H-1,2,4-triazolylmethyl-1'-yl)-2-hydroxy-2-(2'-chloro-4'-bromophenyl)-acetic acid-β-methoxyethyl ester (compound No. 1.32), 2-(1H-1,2,4-triazolylmethyl-1'-yl)-2-hydroxy-2,4-dichlorophenylacetic acid allyl ester (compound No. 1.40), 2-(1H-1,2,4-triazolylmethyl-1'-yl)-2-hydroxy-2-(2'-chloro-4'-bromophenyl)-acetic acid isopropyl ester (compound No. 1.55), 2-(1H-1,2,4-triazolylmethyl-1'-yl)-2-hydroxy-2-(2'-chloro-4'-fluorophenyl)-acetic acid ethyl ester (compound No. 1.101), 2-(1H-1,2,4-triazolylmethyl-1'-yl)-2-hydroxy-2,4-dichlorophenylacetic acid methylthiomethyl ester (compound No. 1.116), 2-(1H-1,2,4-triazolylmethyl-1'-yl)-2-acetoxy-2,4-dichlorophenylacetic acid methyl ester (compound No. 2.2), 2-(1H-1,2,4-triazolylmethyl-1'-yl)-2-acetoxy-2-(2'-chloro-4'-bromophenyl)-acetic acid ethyl ester (compound No. 2.66), 2-(1H-1,2,4-triazolylmethyl-1'-yl)-2-ethoxycarbonyloxy-2,4-dichlorophenylacetic acid methyl ester (compound No. 2.109), 2-(1H-1,2,4-triazolylmethyl-1'-yl)-2-ethoxycarbonyloxy-2-(2'-chloro-4'-bromophenyl)-acetic acid ethyl ester (compound No. 2.132), and 2-(1H-1,2,4-triazolylmethyl-1'-yl)-2-ethoxycarbonyloxy-2-(2'-chloro-4'-fluorophenyl)-acetic acid methyl ester (compound No. 2.157).

The compounds of the formula I can be produced by a whole series of reaction variants A to G, as outlined in two reaction schemes in the following and subsequently described in detail. In the formulae Ia, Ib, Ic, Id, II, III, IV, V, VI, VII, VIII, IX, XI, XII and XIII, the substituents Ar, X, n, $R_1$, $R_2$, $R_3$, $R_4$ and $R_5$ have the meanings given under the formula I.

$R_6^*$ and $R_7^*$ are organyl groups, preferably unsubstituted or substituted $C_1$–$C_8$-alkyl, or phenyl or substituted phenyl. Q in formula VI is one of the customary removal groups, for example halogen, especially chlorine, bromine or iodine; a sulfonyloxy group, particularly benzenesulfonyloxy, paratosyloxy or lower alkylsulfonyloxy, preferably mesyloxy; or an acyloxy group, such as trifluoroacetyloxy. Q is also a hydroxyl group, or, according to "Synthesis" 1979, pp. 561–569, it is the group

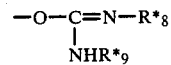

wherein $R_8^*$ and $R_9^*$ are organyl groups, especially lower alkyl, or unsubstituted or substituted phenyl groups. M is hydrogen or a metal atom, particularly an alkali metal atom, preferably sodium or potassium. Hal is halogen, preferably chlorine or bromine. Y is halogen, preferably chlorine or bromine, or it is a sulfate group or a sulfonic acid ester group.

The symbol α denotes representatively the grouping

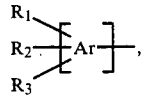

wherein the substituents $R_1$, $R_2$, $R_3$ and Ar are as defined under the formula I.

Az is the following Azolyl group

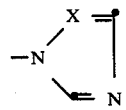

wherein X is —CH= or —N=.

1. Reaction scheme

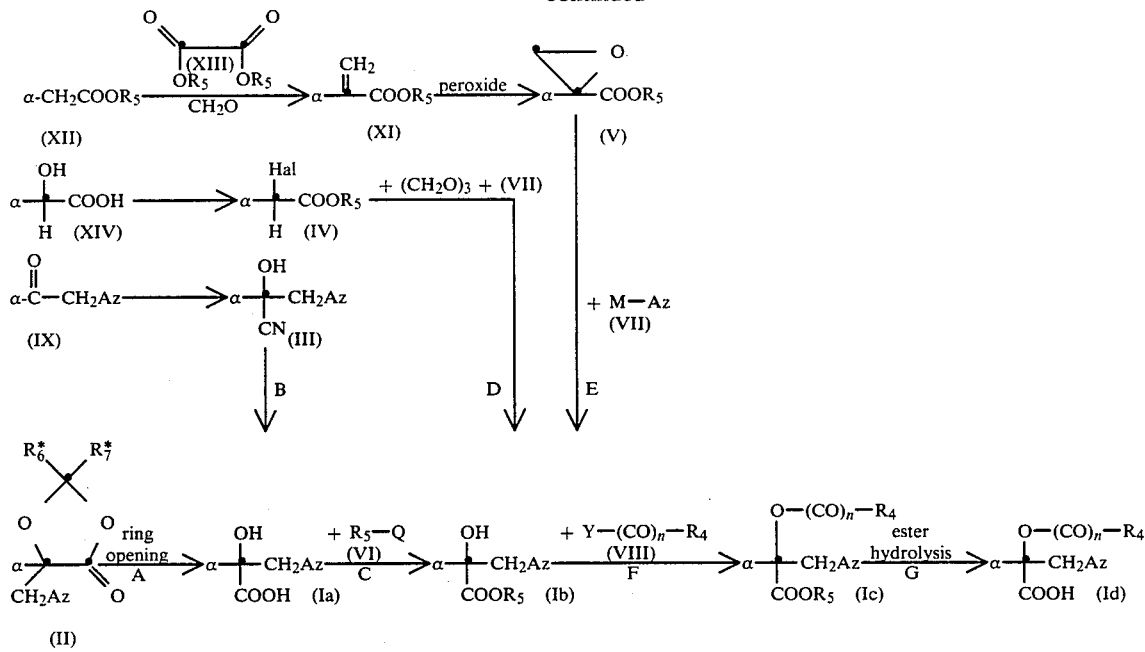

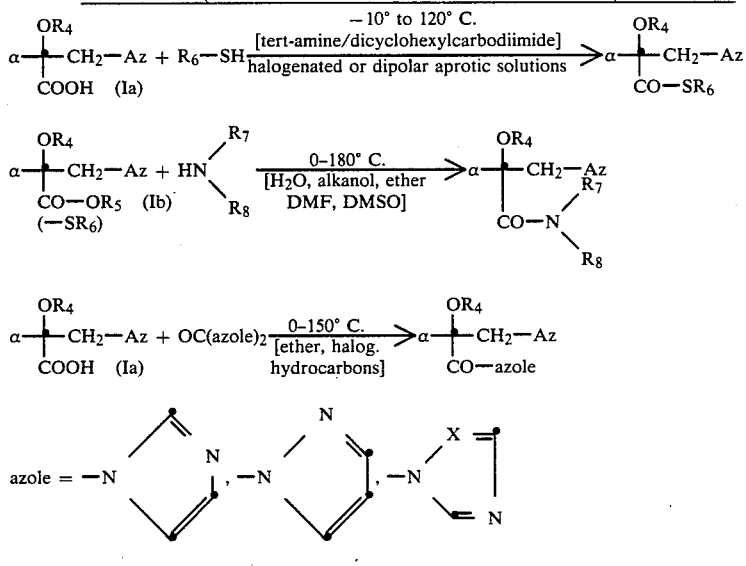

The procedure for producing compounds of the formula I is in detail as follows:

(i) Free α-hydroxycarboxylic acids (=mandelic acids) of the formula Ia are particularly preferred, and they are produced by hydrolysing either according to equation A a dioxolanone of the formula II or according to equation B a cyanohydrin of the formula III (embraced by the formula I) in a basic or acidic medium.

The hydolysis reactions A and B are performed with acids or bases, advantageously in aqueous and/or alcoholic solutions, that is, in polar solvents. The reactions can also be carried out in two-phase media. The addition in this case of a customary phase-transfer catalyst is advantageous. Inorganic and organic acids are suitable, for example: mineral acids, such as hydrohalic acids, sulfuric acid, phosphoric acid or sulfonic acids (p-toluenesulfonic acid, methanesulfonic acid). And suitable bases are organic and inorganic ones, for example: oxides, hydrides, hydroxides, carbonates, carboxylic acid salts and alcoholates of alkaline-earth metals and alkali metals, especially those of sodium and potassium.

The reaction temperatures in the case of the ring-opening reaction A are in general between 0° and +140° C., preferably between +30° and +80° C., and in the case of the hydrolysis of the cyanohydrin III between +60° and +140° C., preferably between +80° and +120° C., or in each case at the boiling point of the solvent or solvent mixture.

Starting compounds of the formula II are for the most part known from the EP Published Specification No. 44276. The new compounds are produced analogously.

The mandelonitriles III (variant B) embraced by the formula I can be prepared, using customary procedures, from aryl-azolylmethyl ketones of the formula IX

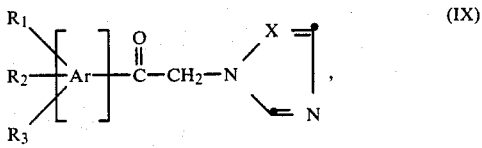

in the manner of a cyanohydrin synthesis, by reaction with HCN or alkali cyanide at 0° to 100° C., advantageously with the addition of small amounts of a base (preferably NH₄OH or NH₃ gas), or by way of the corresponding NaHSO₃ adduct of IX [Org. Syntheses Coll. Vol. I, p. 336, or French Patent Specification No. 2,292,706; cp. also Houben-Weyl "Methoden der organischen Chemie", Vol. 6/3, p. 412].

Mandelonitriles III can also be produced, according to J. Org. Chem. 39, p. 914 (1974), by reaction of IX with trimethylsilyl cyanide, in the presence of catalytic amounts of $ZnJ_2$, and subsequent hydrolysis of the addition product.

They can be produced also by reaction of a ketone IX with a di-lower-alkylcyanohydrin of the formula

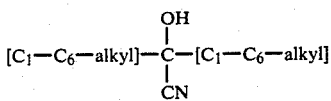

(alkyl is in particular methyl, ethyl or propyl), preferably in an inert solvent, or without solvent, at 50°–150° C.

The hydrolysis of the nitriles III to mandelic acid derivatives of the formula Ia can be performed by methods analogous to known methods, for example with concentrated hydrochloric acid [Houben-Weyl "Methoden der organischen Chemie", Vol. VIII, p. 427 ff. (1952)].

The ketones of the formula IX, serving as intermediates, have in part become known from the German Offenlegungsschrift No. 2,431,407 or from the GB Patent Specification No. 1,464,224. Ketones of this type can be obtained also by hydrolysis from corresponding ketals, for example from those which are mentioned in any one of the following publications: German Offenlegungsschriften Nos. 2,610,022, 2,602,770, 2,930,029, 2,930,196 and 2,940,133.

Ketones of the formula IX which have not been described can be obtained by one of the aforementioned published methods.

(ii) Mandelic acid esters of the formula Ib are particularly preferred. They can be produced according to equation C, in the customary manner, by esterification of the corresponding mandelic acid derivative Ia (also in the form of its alkali metal salt) with R₅-Q (VI) at −20° to +140° C. Aprotic solvents are preferred for this reaction. The direct esterification is advantageously performed with excess alcohol R₅-OH at 0° to 80° C. in the presence of mineral acids, or preferably of Lewis acids, such as boron trifluoride etherate. Mandelic acid esters of the formula Ib can be prepared also according to equation D from an α-haloacetic acid ester of the formula IV with paraformaldehyde at 0° to 140° C., preferably at 10° to 80° C., and (a) with the desired azole of the formula VII (i.e. imidazole or triazole) in the presence of a base (for example sodium hydride), or (b) with the alkali salt of the azole VII in anhydrous solvents (for example dimethyl sulfoxide). The last-mentioned method is a particular aspect of the present invention.

Esters of the formula IB can be produced also according to equation E from oxiranes of the formula V with an azole VII (M=H or alkali metal), in an inert, preferably polar solvent (DMF, acetonitrile, DMSO and others, also in admixtures with hydrocarbons), at 20° to 100° C. Inorganic or organic bases can in this case be added [cp. also EP Published Specification No. 15756].

As outlined in the 1st reaction scheme, oxiranes of the formula V are obtainable by customary epoxidation (for example $H_2O_2$/aqueous NaOH, peracetic acid, and so forth) from corresponding alkenyl compounds of the formula XI. Compounds of the formula XI are produced from arylacetic acid esters of the formula XII by reaction with oxalic acid esters of the formula XIII and formaldehyde in the presence of a base [cp. Helvetica Chimica Acta 30, p. 1349 (1947) and German Offenlegungsschrift No. 2,653,189].

Esters of the formula IB can also be produced from acids of the formula Ia and dimethylformamide acetal (preferably in excess), the acetal component of which is intended to form the alcoholic part of the ester, in solvents (for example a similar anhydrous alcohol or an ether at 0° to 160° C. [Angew. Chemie 75, p. 296 (1963) and Helv. Chim. Acta 48, 1747 (1965)].

(iii) The thioesters corresponding to the formula Ib and stated in the 2nd reaction scheme can be produced from the acids IA with thioalcohols, in the presence of weak bases (tert-amines), in aprotic solvents, such as CHCl₃, DMF, dichloromethane, DMSO, and so forth, at −10° to +120° C., preferably at 0° to +40° C. There are obtainable from esters (or thioesters) of the formula Ib, with excess amine R₇-NH-R₈, corresponding mandelic acid amides and mandelic acid hydrazides. When R₇ and R₈ are closed to form a 5- or 6-membered ring, a heterocycle of this kind is introduced advantageously by reaction of the acid Ia with 1,1′-carbonyldi-azole or -azine at 0° to 150° C., preferably in solvents such as ethers or halogenated hydrocarbons.

(iv) The free hydroxyl group in the compounds Ia and Ib can be subjected to the customary etherification and esterification reactions, such as are familiar to every expert. The acrylation step is suitably carried out (n−1 in the formula I) in the presence of sodium hydride or of a mixture of a customary tert. amine with catalytic amounts of 4-dialkylamino-pyridine (for example 4-dimethylaminopyridine). Acrylation can then be performed as a rule at room temperature [Angew. Chemie 90, p. 615 (1978), and "Synthesis" 1972, p. 619].

Conversely, it is possible with such acrylated compounds to perform hydrolysis reactions for the formation of the free OH group, as well as transesterification reactions.

All production variants described in the foregoing under (i) (ii), (iii) and (iv) form subject matter of the present invention.

The remaining starting products of the formulae IV, VI, VII, VIII, XI, XII and XIII are known, or are produced by methods known per se.

The compounds of the formula I each contain, in the position adjacent to the aromatic group Ar and to R, an asymmetric centre (*)

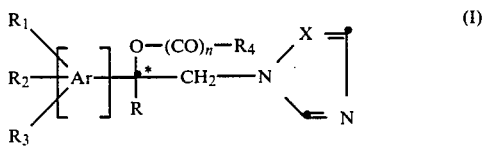

and can therefore be present in two enantiomeric forms. There is generally formed in the production of these substances a mixture of both enantiomters; and this can then be separated, in the customary manner, for example by fractional crystallisation, into the optical antipodes. Optically pure antipodes are obtained for example, according to process variant D, by converting an optically pure α-hydroxicarboxylic acid of the formula (XIV) into the optically pure compound of the formula IV, and reacting this, as under the variant D, to give the ester Ib.

Reference to a compound of the formula I denotes, except where otherwise stated, a mixture of both enantiomeric forms. Both antipodes exhibit differing microbicidal activity.

It has been found that compounds of the formula I surprisingly exhibit, for practical requirements, a very favourable microbicidal spectrum against phytopathogenic fungi and bacteria. The compounds of the formula I thus have very advantageous curative, preventive and systemic properties, and can be used for the protection of cultivated plants. The microorganisms occurring on plants or on parts of plants (fruit, blossom, foliage, stalks, tubers or roots) of various cultivated crops can be inhibited or destroyed with the active substances of the formula I, and also parts of plants subsequently growing remain preserved from such microorganisms. The active substances are effective against the phytopathogenic fungi belonging to the following classes: Ascomycetes (for example Venturia, Podosphaera, Erysiphe, Monilinia and Uncinula); Basidiomycetes (for example the species Hemileia, Rhizoctonia, Pellicularia and Puccinia); Fungi imperfecti (for example Botrytis, Helminthosporium, Fusarium, Septoria, Cercospora, Piricularia and Alternaria) and Phycomycetes, such as Pythium. Furthermore, the compounds of the formula I have a systemic action. They can also be used as dressing agents for the treatment of seed (fruits, tubers and grain), and of plant cuttings to protect them from fungus infections, and also against phytopathogenic fungi occurring in the soil. The active substances according to the invention are distinguished also by a particularly good tolerance to cultivated plants.

The present invention thus relates to microbicidal compositions, and to the use of the compounds of the formula I for combating phytopathogenic microorganisms, especially fungi which damage plants, and for preventing an infestation of plants.

In addition, the present invention relates also to the production of agrochemical compositions, whereby the active substance concerned is intimately mixed together with one or more substances or groups of substances described herein. Also included is a process for treating plants, which comprises the application of the compounds of the formula I or of the novel compositions.

Within the scope of this invention, target crops with respect to the range of indications disclosed herein include for example the following species of cultivated plants: cereals: (wheat, barley, rye, oats, rice, sorghum and related cereals); beet: (sugar beet and fodder beet); pomaceous fruit, stone fruit and soft fruit: (apples, pears plums, peaches, almonds, cherries, strawberries, rasberries and blackberries); legumes: (beans, lentils, peas and soya-bean); oil plants: (rape, mustard, poppy, olives, sunflowers, coco, castor-oil plants, cocoa and groundnuts); Cucurbitacea: (pumpkins, cucumbers and melons); fibre plants: (cotton, flax, hemp and jute); citrus fruits: (oranges, lemons, grapefruit and mandarins); varieties of vegetables: (spinach, lettuce, asparagus, varieties of cabbage, carrots, onions, tomatoes, potatoes and paprika); laurel plants: (avocado, cinnamon and camphor); or plants such as maize, tobacco, nuts, coffee, sugar beet, tea, grapevines, hops, bananas and natural rubber plants; and also ornamental plants.

Active substances of the formula I are customarily used in the form of compositions, and can be applied, simultaneously or successively, with further active substances to the area or plants to be treated. These further active substances can be fertilisers, trace-element agents or other preparations influencing plant growth. They can however also be selective herbicides, insecticides, fungicides, bacteriacides, nematicides or molluscicides, or mixtures of several of these preparations, optionally together with carriers commonly used in formulation practice, tensides or other additives factilitating application.

Suitable carriers and additives can be solid or liquid and they correspond to the substances customarily employed in formulation practice, for example natural or regenerated mineral substances, solvents, dispersing agents, wetting agents, adhesives, thickeners, binders or ferilisers.

The compounds of the formula I are used either in an unmodified form or preferably together with auxiliaries customarily employed in formulation practice, and are thus processed in a known manner for example into the form of emulsion concentrates, brushable pastes, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objectives to be achieved and the given conditions. Favourable applied amounts are in general between 50 g and 5 kg of active substance (AS) per hectare, preferably between 100 g and 2 kg of AS per hectare, and in particular between 200 g and 600 g of AS per hectare.

Preparations of the types mentioned can be applied directly to the plants or parts of plants (leaf application), to the locus of the plants (soil application) or to the propagation parts, for example by means of seed application.

The formulations, that is to say, the compositions or preparations containing the active substance of the formula I and optionally a solid or liquid additive, are produced in a known manner, for example by the intimate mixing and/or grinding of the active substances with extenders, such as with solvents, solid carriers and optionally surface-active compounds (tensides). Such preparations likewise form subject matter of the present invention.

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethylene glycol monomethyl ether, ketones, such as cyclohexanone, strongly polar solvents, such as N-methyl-2-pyrrolidone, dimethyl sulfoxide of dimethylformamide, and also optionally epoxidised vegetable oils or soybean oil; or water.

The solid carriers used, for example for dusts and dispersible powders, can be calcite, talcum, kaolin, montmorillonite or attapulgite, highly dispersed silicic acid or highly dispersed absorbent polymers. Suitable granulated adsorptive carriers are pumice, ground brick, sepiolite or bentonite; and suitable nonsorbent carriers are for example calcite or dolomite. It is also possible to use ground plant residues.

Suitable surface-active compounds are, depending on the nature of the active substance of the forumla I to be formulated, nonionic, cationic and/or anionic tensides having good emulsifying, dispersing and wetting properties. By 'tensides' are also meant mixtures of tensides.

The tensides customarily used in formulation practice are described, inter alia, in the following publications:

"Mc Cutcheon's Detergents and Emulsifiers Annual", MC Publishing Corp., Ringwood, N.J. 1980, and Sisely and Wood, "Encyclopedia of Surface Active Agents", Chemical Publishing Co., Inc. New York, 1980.

The agrochemical preparations contain as a rule 0.1 to 99%, particularly 0.1 to 95%, of active substance of the formula I, 99.9 to 1%, especially 99.8 to 5%, of a solid or liquid additive, and 0 to 25%, in particular 0.1 to 25%, of a tenside. Whereas commercial products are preferably in the form of concentrated compositions, the compositions employed by the end-user are as a rule diluted.

The compositions can also contain further additives, such as stabilisers, antifoam agents, viscosity regulators, binders and adhesives, as well as fertilisers or other active substances for obtaining special effects.

The following Examples serve to further illustrate the invention without limiting the scope thereof. Temperature values are given in degrees Centigrade, and percentages and 'parts' relate to weight. In addition, the following symbols are used: h=hour; d=day; min=minute; RT=room temperature; N=normality; abs=absolutely anhydrous; DMSO=dimethyl sulfoxide; DMF=dimethylformamide.

PRODUCTION EXAMPLES

Example 1

(Variant A in the 1st reaction scheme)

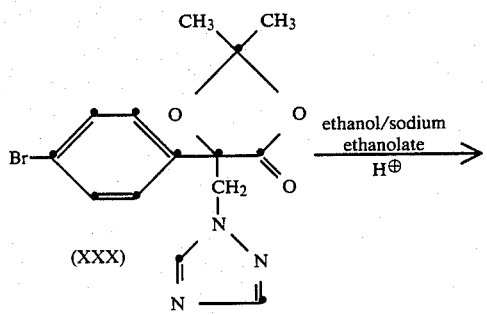

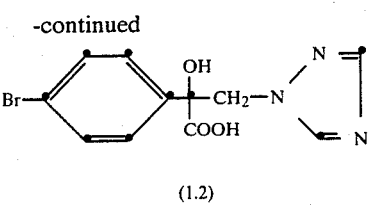

(1.2)

Production of 2-(1,2,4-triazolylmethyl-1'-yl)-2-hydroxy-4-bromophenylacetic acid (Compound No. 1.2)

7.0 g (0.02 mol) of 4-(1H-1,2,4-triazolylmethyl)-4-(4-bromophenyl)-2,2-dimethyl-1,3-dioxolan-5-one are added to a solution of 0.5 g (0.022 mol) of sodium in 50 ml of abs. ethanol, and the mixture is refluxed with stirring for 4 hours. The formed suspension is acidified with dilute hydrochloric acid; it is then concentrated by evaporation, digested with a small amount of water, filtered off and dried; yield=5.0 g (80% theory); m.p. 238°–239° C.

EXAMPLE 2

(Variant C)

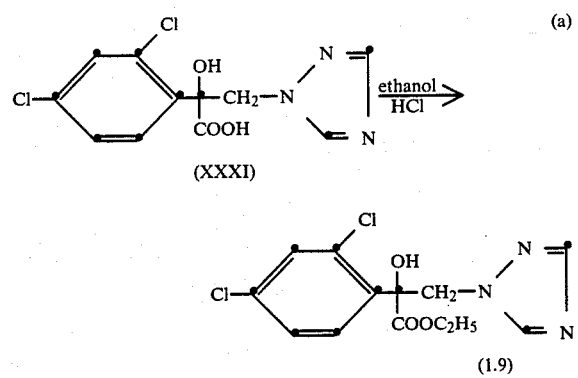

Production of 2-(1,2,4-triazolylmethyl-1'-yl)-2-hydroxy-2,4-dichlorophenylacetic acid ethyl ester (Compound No. 1.9)

50 g (0.165 mol) of 2-(1H-1,2,4-triazolylmethyl-1'-yl)-2-hydroxy-2,4-dichlorophenylacetic acid are suspended in 500 ml of absolute ethanol. The suspension is kept at a temperature of 20° to 30° C., and saturated, with stirring, with hydrogen chloride. The reaction mixture is stirred for 6 days at room temperature; it is subsequently refluxed for 4 hours and then concentrated by evaporation, and the residue is rendered slightly alkaline, with cooling, by means of 10% aqueous sodium hydroxide solution (pH=8 to 9). The occurring precipitate is filtered off, dissolved in methylene chloride and washed with water. The organic phase is dried over sodium sulfate, filtered and then concentrated by evaporation. The crystalline residue is recrystallised from methylene chloride, m.p. 121°–123° C.

Instead of a saturation of the starting suspension with HCl gas, the reaction can be catalysed by the addition of 47.2 g (0.33 mol) of boron trifluoride etherate.

(b) Production of
2-(1H-1,2,4-triazolylmethyl-1'-yl)-2-hydroxy-4-bromo-phenylacetic acid methyl ester and of the methoiodide thereof 62.4 g (0.2 mol) of 2-(1H-1,2,4-triazolylmethyl-1'-yl)-2-hydroxy-4-bromophenylacetic acid are stirred up with 200 ml of 1N NaOH and 400 ml of methanol; the mixture is then concentrated in vacuo and dried under high vacuum. The formed sodium salt is taken up in 500 ml of abs. DMF, and 42.6 g of methyl iodide are added dropwise with cooling, and stirring is maintained for 40 hours at room temperature. The reaction mixture is then concentrated in vacuo, and the residue is distributed between water and methylene chloride. The organic phase is washed with water, dried over sodium sulfate and concentrated by evaporation, and the residue is digested with diethyl ether, m.p. 108°–109° C. (Compound No. 1.3).

The aqueous phase obtained above is concentrated by evaporation; the residue is taken up in chloroform, washed with a small amount of water, dried over sodium sulfate, filtered and concentrated by evaporation. The new residue is dissolved in chloroform, and is caused to crystallise by the addition of diethyl ether. The methoiodide which has precipitated is filtered off and washed with diethyl ether, m.p. 150°–157° C. (Compound No. 6.1).

(c) Production of
2-(1H-1,2,4-triazolylmethyl-1'-yl)-2-hydroxy-2-(2',4'-dichlorophenyl)-acetic acid methyl ester (Compound No. 1.1)

6.0 g (0.02 mol) of 2-(1H-1,2,4-triazolylmethyl-1'-yl)-2-hydroxy-2,4-dichlorophenylacetic acid (XXXI) are dissolved in 120 ml of abs. methanol, and 10 ml of freshly distilled thionyl chloride are added dropwise, with cooling, in the course of 20 minutes, and a colourless precipitate is formed. The reaction mixture is refluxed for 14 hours and then concentrated by evaporation; the residue is subsequently rendered alkaline, with cooling, by means of saturated aqueous sodium hydrogen carbonate solution, and extracted with methylene chloride. The extracts are washed with water, dried over sodium sulfate and concentrated by evaporation, and the residue [m.p. 185°–188° C.] is recrystallised from acetone, m.p. 188°–190° C.

5 ml (0.04 mol) of boron trifluoride etherate can be advantageously used in place of $SOCl_2$.

(d) (Variant F acrylation)

Production of
2-(1H-1,2,4-triazolylmethyl-1'-yl)-2-acetoxy-2-(2',4'-dichlorophenyl)-acetic acid methyl ester (Compound No. 2.2)

6.4 g (0.02 mol) of the compound No. 1.1 obtained under (c) are placed together with 4.1 ml of triethylamine and 0.5 g of 4-dimethylaminopyridine into 40 ml of dichloromethane. At room temperature are added dropwise 3.4 ml of acetic anhydride in 5 ml of dichloromethane, in the course of which the suspension heats up from 22° to 26° C. and, after completion of the dropwise addition, goes into solution. Ice-water is added after 48 hours, and extraction is performed with dichloromethane. The extracts are washed with water, dried, and concentrated by evaporation to leave a brownish oil, which is purified through silica gel (diethyl ether). The yield is 4.8 g of the compound No. 2.2, m.p. 143°–144° C.

EXAMPLE 3

(Variant F-etherification)

Production of
2-(1H-1,2,4-triazolylmethyl-1'-yl)-2-methoxy-4-bromo-phenylacetic acid methyl ester (Compound No. 3.32)

A solution of 2.3 g (0.1 mol) of sodium in 200 ml of abs. methanol is added portionwise to 15.9 g (0.051 mol) of 2-(1H-1,2,4-triazolylmethyl-1'-yl)-2-hydroxy-4-bromophenylacetic acid (Compound No. 1.2). The reaction mixture is slowly heated, refluxed for a short time (5–10 min), and then evaporated to dryness in vacuo. The residue is taken up in 200 ml of abs. DMF, and at 0° to +5° C. are added, within half an hour, 29 g of methyl iodide, and the mixture is stirred for about 10 hours at room temperature; the solvent is subsequently removed in vacuo, and ice-water is added to the residue, and extraction is performed with diethyl ether. The organic phase is washed with water, dried over sodium sulfate, filtered off and concentrated by evaporation. The residue is recrystallised from diethyl ether, m.p. 80°–92° C.

Methoiodide can be isolated from the aqueous phase in a manner analogous to that of Example 2b (Comp. No. 6.4).

EXAMPLE 4

(Variant B)

(a) Production of the cyanohydrin of
2,4-dichlorophenyl-(1H-1,2,4-triazolylmethyl-1'-yl)-ketone 38.4 g (0.15 mol) of the starting ketone are dissolved in 80 ml (0.88 mol) of acetone cyanohydrin at about 40° C. After the solution has cooled, after about 1 hour, to room temperature, 4 drops of concentrated aqueous ammonia solution are added, whereupon a clouding of the reaction solution occurs. The reaction mixture is stirred for about 10 hours at room temperature, and then allowed to stand for 1 day. The formed precipitate is subsequently filtered off and dried, m.p. 145° C., with the decomposition (Compound No. 10.1).

$^1$H-NMR (CDCl$_3$+DMSO-d$_6$) [δ in ppm] 4.9 (d, 2H), —CH$_2$—; 7.1–7.6 (m,3H), phenyl-H; 7.7 and 8.3 each (S,1H), azole-H.

(b) Production of
2-(1H-1,2,4-triazolylmethyl-1'-yl)-2-hydroxy-2,4-dichlorophenylacetic acid (Compound No. 1.4)

To 20 g of the cyanohydrin No. 10.1 produced according to (a) are added 200 ml of concentrated hydrochloric acid, and a preciptate is formed. The reaction mixture is heated to boiling; after 20 hours are added a further 100 ml of concentrated hydrochloric acid, and refluxing is maintained for 24 hours. The mixture is then concentrated in vacuo; and the solid residue is taken up in 200 ml of water, whereupon a solution is firstly observed and subsequently again a precipitate. The pH value of the solution is adjusted to about 2 by the addition of concentrated aqueous ammonia solution, and the mixture is homogenised in a mixer; the precipitate is then filtered off, washed with water and dried. The crude product, melting at 154°–165° C., can be either further reacted or be purified by recrystallisation from acetone. The purified product melts at 177°–181° C.

EXAMPLE 5

(Variant D)

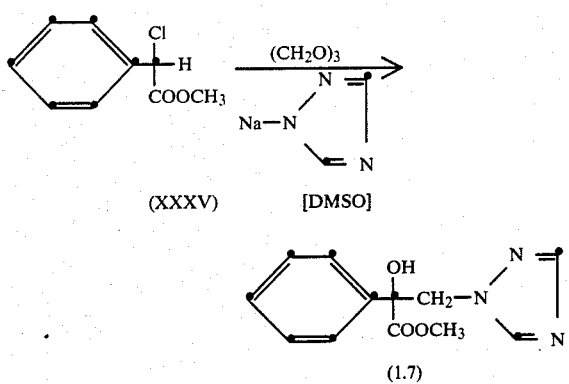

(a) Production of 2-(1H-1,2,4-triazolylmethyl-1'-yl)-2-hydroxyphenylacetic acid methyl ester (Compound No. 1.7)

2.4 g of sodium hydride (55% oil dispersion) are added dropwise, in a nitrogen atmosphere and with stirring, to 3.8 g (0.055 mol) of 1H-1,2,4-triazole dissolved in 20 ml of abs. DMSO. After the vigorous evolution of hydrogen has subsided, the mixture is heated for half an hour at 60° C., and is subsequently cooled to room temperature; 2 g of solid paraformaldehyde are firstly added, and afterwards there is added dropwise, at 15°–20° C. with ice-water cooling, a solution of 9.2 g (0.05 mol) of α-chlorophenylacetic acid methyl ester in 5 ml of DMSO. The mixture is stirred for 15 hours at room temperature; is is then heated and kept at 60° C. for 6 hours. After the addition of a further 2 g of paraformaldehyde, the mixture is heated at 80° C. for a further 5 hours, and is afterwards cooled; ice-water is added and extraction is performed with methylene chloride. The extracts are washed with water, dried over sodium sulfate, filtered and concentrated by evaporation. Excess DMSO is removed at about 60° C. under high vacuum. The product is chromatographically purified [silica gel, chloroform/diethyl ether (1:1); towards the end with the addition of 20% of methanol]. The yield is 5.0 g, m.p. 104°–106° C.

EXAMPLE 6

Production of N-methyl-[2-(1H-1,2,4-triazolylmethyl-1'-yl)-2-hydroxy-2-(2',4'-dichlorophenyl]-acetamide (Compound No. 5.2)

20 g (0.0632 mol) of the compound No. 1.1 are suspended in 40 ml of methanol; 39.3 g of methylamine solution (40%, aqueous) and a spatula tip of 1,4-diazabicyclo[2.2.2]octane are added, and the mixture is stirred for 12 days at room temperature. It is then concentrated by evaporation, ice-water is added, and the pH value is adjusted to 6 with 2N hydrochloric acid, the mixture is subsequently filtered, and the residue is recrystallised from isopropanol, m.p. 157° C.

EXAMPLE 7

Production of 2-hydroxy-2-(2',4'-dichlorophenyl)-2-(1H-1,2,4-triazolylmethyl-1'-yl)-acetic acid allyl ester (Compound No. 1.40)

18.0 g (0.06 mol) of the compound No. 1.4 are suspended in 140 ml of abs. dichloromethane, and a solution of 15.3 g of N,N-dimethylformamide-diallylacetal in 60 ml of dichloromethane is added with ice cooling. The formed solid mixture is refluxed for 7 hours, and then concentrated by evaporation. The residue is purified through silica gel (chloroform/diethyl/ether 1:1). From the eluate, concentrated by evaporation, are obtained with hexane 15.0 g of the white final product, m.p. 106°–108° C.

EXAMPLE 8

(a) Production of

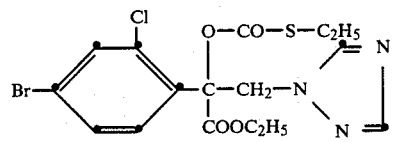

2-(2'-Chloro-4'-bromophenyl)-2-(ethylthiocarbonyloxy)-2-(1H-1,2,4-triazolylmethyl-1'-yl)-acetic acid ethyl ester (Compound No. 2.149)

1.3 g (0.03 mol) of 55% sodium hydride dispersion in paraffin oil are placed into 30 ml of tetrahydrofuran. There are then added dropwise, in a nitrogen atmosphere at room temperature, 11.2 g (0.03 mol) of the corresponding 2-(2'-chloro-4'-bromophenyl)-2-hydroxy-2-(1H-1,2,4-triazolylmethyl-1'-yl)-acetic acid ethyl ester dissolved in 70 ml of tetrahydrofuran. After completion of the evolution of hydrogen, 4.5 g (0.036 mol) of chlorothioformic acid-S-ethyl ester are added dropwise at 0°–5° C., and the reaction mixture is stirred overnight at room temperature. After concentration in a water-jet vacuum, the residue is dissolved in ethyl acetate, and washed with an ice-cooled sodium carbonate solution and water. The residue is then dried with sodium sulfate, filtered and concentrated by evaporation; it is subsequently dissolved in acetonitrile for separation of the paraffin oil, and the oil is removed in a separating funnel. The yield after concentration in a water-jet vacuum is 8.5 g of final product in the form of yellow oil.

(b) By using 3.9 g (0.036 mol) of dimethylcarbamoyl chloride in place of the chlorothioformic acid-S-ethyl ester, with otherwise the same procedure, there are obtained 10.8 g of 2-(2'-chloro-4'-bromophenyl)-2-(N,N-dimethylcarbamoyloxy)-2-(1H-1,2,4-triazolylmethyl-1'-yl)-acetic acid ethyl ester, m.p. 45°–66° C. (Compound No. 2.181).

EXAMPLE 9

(a) Production of 2-(2',4'-dichlorophenyl)-2-hydroxy-2-(1H-1,2,4-triazolylmethyl-1'-yl)-acetic acid thioethyl ester (Compound No. 4.3)

12.1 g (0.04 mol) of 2-(1H-1,2,4-triazolylmethyl-1'-yl)-2-hydroxy-2,4-dichlorophenylacetic acid together with 3.0 ml (0.0406 mol) of ethyl mercaptan and 0.5 g of 4-dimethylaminopyridine are placed into 60 ml of abs. DMF at 0° C. There are then added dropwise, with stirring, 8.2 g of dicyclohexylcarbodiimide dissolved in 25 ml of abs. DMF; the mixture is stirred for 15 hours, subsequently filtered, and the residue is washed with DMF. Ice-water is added to the filtrate, and the glutinous substance which precipitates is taken up in dichloromethane, and the aqueous phase is further extracted with dichloromethane. The combined extracts are washed with water, dried, and concentrated by evaporation. The solid residue is recrystallised from tetrahydrofuran/ethyl acetate to give a yield of 7.5 g (55%) of final product, m.p. 180°–182° C.

(b) By using 4.5 ml of thiophenol in place of the ethyl mercaptan, with otherwise the same procedure, and recrystallisation of the final product from tetrahydrofuran/hexane, there are obtained 5.5 g of 2-(2',4'-dichlorophenyl)-2-hydroxy-2-(1H-1,2,4-triazolylmethyl-1'-yl)-acetic acid-thiophenyl ester (Compound No. 4.7) in the form of white crystals, m.p. 164°–166° C.

The following compounds according to the present invention can be produced in the manner of the Examples given in the foregoing and of the production variants described earlier in the text:

TABLE 1

Compounds of the formula

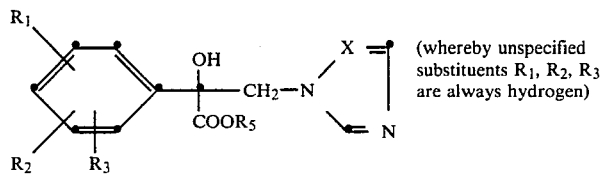

(whereby unspecified substituents $R_1$, $R_2$, $R_3$ are always hydrogen)

| Comp. No. | $R_1, R_2, R_3$ | $R_5$ | X | Physical data [m.p.] |
|---|---|---|---|---|
| 1.1 | 2,4-Di—Cl | $CH_3$ | N | m.p. 188–190° C. |
| 1.2 | 4-Br | H | N | 238–239° C. |
| 1.3 | 4-Br | $CH_3$ | N | 108–109° C. |
| 1.4 | 2,4-Di—Cl | H | N | 177–181° C. |
| 1.5 | 4-Br | $C_4H_9$—n | N | 74–76° C. |
| 1.6 | 4-Br | $C_2H_5$ | N | 108–112° C. |
| 1.7 | H | $CH_3$ | N | 104–6° C. |
| 1.8 | 2,4-Di—Cl | $C_2H_5$ | CH | 136–9° C. |
| 1.9 | 2,4-Di—Cl | $C_2H_5$ | N | 121–123° C. |
| 1.10 | 2,4-Di—Cl | $C_3H_7$—n | N | 115–116° C. |
| 1.11 | 2,4-Di—Cl | $C_3H_7$—n | CH | |
| 1.12 | 2,4-Di—Cl | $C_3H_7$—i | N | 146–149° C. |
| 1.13 | 2,4-Di—Cl | $C_4H_9$—n | CH | |
| 1.14 | 2,4-Di—Cl | $C_4H_9$—n | N | 77–80° C. |
| 1.15 | 4-Cl | $C_3H_7$—n | N | |
| 1.16 | 2,4-Di—Cl | —$CH(CH_3)C_3H_7$—n | N | oil |
| 1.17 | 2,4-Di—Cl | (cyclohexyl) | N | semisolid substance |
| 1.18 | 2,4-Di—Cl | (cyclopentyl) | N | m.p. 92–97° C. |
| 1.19 | 2,4-Di—Cl | —$CH_2$—$C_6H_5$ | N | m.p. 151–152° C. |
| 1.20 | 2,4-Di—Cl | —$CH_2$—$C_6H_5$ | CH | |
| 1.21 | 2,4-Di—Cl | —$C_6H_4Cl(4)$ | N | |
| 1.22 | 3-$NO_2$ | $CH_3$ | N | |
| 1.23 | 2,4-Di—Cl | $C_6H_3Cl_2(2,4)$ | N | |
| 1.24 | 2,4-Di—Cl | —$C(CH_3)_3$ | N | m.p. 126–128° C. |
| 1.25 | 2,4-Di—Cl | $C_6H_3Cl_2(2,4)$ | CH | |
| 1.26 | 3-$CF_3$ | $CH_3$ | N | |
| 1.27 | 2-Cl, 4-Br | $CH_3$ | N | m.p. 165–172° C. |
| 1.28 | 2-Cl, 4-Br | $C_2H_5$ | CH | |
| 1.29 | 2-Cl, 4-Br | $C_2H_5$ | N | m.p. 132–139° C. |
| 1.30 | 2,3,4 Tri—Cl | $CH_3$ | N | |
| 1.31 | 4-Cl | $C_2H_5$ | N | m.p. 60–4° C. |
| 1.32 | 2-Cl—4-Br | $CH_2CH_2OCH_3$ | N | m.p. 167–171° C. |
| 1.33 | 2-Cl—4-Br | $CH_2CH_2OCH_3$ | CH | |
| 1.34 | 2,4-Di—Cl | $CH_2CH_2OCH_3$ | N | |
| 1.35 | 2-Cl, 4-F | $CH_2CH_2OCH_3$ | N | |
| 1.36 | 2,4-Di—Cl | $CH_2OCH_3$ | N | |
| 1.37 | 2-Cl, 4-Br | $CH_2OCH_3$ | CH | |
| 1.38 | 2-Cl, 4-F | $CH_2SCH_3$ | N | |
| 1.39 | 2-Cl, 4-Br | $CH_2CH=CH_2$ | N | |
| 1.40 | 2,4-Di—Cl | $CH_2CH=CH_2$ | N | m.p. 106–108° C. |
| 1.41 | 2,4-Di—Cl | $CH_2C\equiv CH$ | N | |

TABLE 1-continued

Compounds of the formula (whereby unspecified substituents $R_1$, $R_2$, $R_3$ are always hydrogen)

| Comp. No. | $R_1, R_2, R_3$ | $R_5$ | X | Physical data [m.p.] |
|---|---|---|---|---|
| 1.42 | 2-Cl, 4-Br | $CH_2C \equiv CH$ | N | |
| 1.43 | 2,4-Di—Cl | $-CH_2-\triangle$ (cyclopropyl) | N | m.p. 98–100° C. |
| 1.44 | 2,4,6-Tri—Cl | $CH_3$ | N | |
| 1.45 | 2-F | $CH_3$ | N | |
| 1.46 | 4-Cl | $C_2H_5$ | CH | |
| 1.47 | 3,4-Di—Cl | $C_2H_5$ | N | |
| 1.48 | 2,5-Di—$CH_3$ | $CH_3$ | N | m.p. 135–139° C. |
| 1.49 | 2,4-Di—$CH_3$ | $CH_3$ | N | |
| 1.50 | 2-Cl, 4-F | $CH_2OCH_3$ | N | |
| 1.51 | 2-Cl, 4-F | $C(CH_3)_3$ | N | |
| 1.52 | 2-Cl, 4-Br | $C(CH_3)_3$ | N | |
| 1.53 | 2,4-Di—Cl | $-CH(CH_3)C_2H_5$ | CH | |
| 1.54 | 2,4-Di—Br | $-CH(CH_3)_2$ | N | |
| 1.55 | 2-Cl, 4-Br | $CH(CH_3)_2$ | N | m.p. 150–155° C. |
| 1.56 | 2-Cl, 4-F | $C_3H_{7-n}$ | N | |
| 1.57 | 2,4-Di—Cl | $C_5H_{11-n}$ | N | |
| 1.58 | " | $C_6H_{13-n}$ | N | m.p. 81–82° C. |
| 1.59 | 2,4-Di—Br | $CH(CH_3)C_5H_{11-n}$ | N | |
| 1.60 | 2,4-Di—Cl | $CH(CH_3)COOCH_3$ | N | m.p. 79–81° C. |
| 1.61 | " | $CH_2COOCH_3$ | N | |
| 1.62 | " | $CH_2CH_2SCH_3$ | N | |
| 1.63 | " | $CH_2CH_2Br$ | N | m.p. 180–182° C. |
| 1.64 | " | $C_6H_5$ | N | |
| 1.65 | 2-Cl, 4-Br | $C_6H_3Cl_2(2,4)$ | N | |
| 1.66 | 2-Cl, 4-F | $C_6H_3(CH_3)_2(2,4)$ | N | |
| 1.67 | 2,4-Di—Cl | $C_6H_2(CH_3)_2(3,5)Cl(4)$ | N | |
| 1.68 | " | $C_6H_4(OCH_3)(4)$ | N | |
| 1.69 | " | $C_6H_4Br(3)$ | CH | |
| 1.70 | " | $C_6H_4-C(CH_3)_3(4)$ | N | |
| 1.71 | " | $C_6H_4-CF_3(3)$ | CH | |
| 1.72 | 2-Cl, 4-Br | $-CH_2-$(tetrahydropyran-O) | N | oil |
| 1.73 | 2,4-Di—Br | $-CH_2-$(dihydrothiophene-S) | N | |
| 1.74 | 2,4-Di—Cl | $-CH_2COOC_2H_5$ | N | |
| 1.75 | " | $-CH_2CCl_3$ | N | |
| 1.76 | 2,4-Di—Cl | $-CH_2-C(CH_3)_3$ | N | m.p. 158–160° C. |
| 1.77 | " | $-C_8H_{17}-n$ | N | resin |
| 1.78 | " | $-C_{12}H_{25}-n$ | N | oil |
| 1.79 | " | $-CH_2-CO-C(CH_3)_3$ | N | m.p. 70–73° C. |
| 1.80 | " | $-CH_2-CO-C_6H_3Cl_2(2,4)$ | N | |

TABLE 1-continued

Compounds of the formula

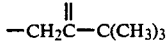  (whereby unspecified substituents R₁, R₂, R₃ are always hydrogen)

| Comp. No. | R₁, R₂, R₃ | R₅ | X | Physical data [m.p.] |
|---|---|---|---|---|
| 1.81 | 2-Cl, 4-Br | —CH₂C(=O)—C(CH₃)₃ | N | |
| 1.82 | 2-Cl, 4-Br | —C₈H₁₇—n | CH | |
| 1.83 | 2-Cl, 4-Br | —CH₂—C₆H₅ | N | m.p. 138–141° C. |
| 1.84 | 2-Cl, 4-F | —CH₂—C₆H₅ | N | |
| 1.85 | " | —CH₂CH=CH₂ | N | |
| 1.86 | " | —CH₂— (cyclopropyl) | CH | resin |
| 1.87 | " |  | N | |
| 1.88 | 2,4-Di—Cl |  | N | |
| 1.89 | 4-Br | —CH₂—CCl₃ | N | |
| 1.90 | 2-Cl, 4-F | —CH₂COOCH₃ | N | |
| 1.91 | 2,4-Di—CH₃ | —CH(CH₃)—COOCH₃ | N | |
| 1.92 | 2-Cl, 4-Br | —CH₂CH₂SCH₃ | N | |
| 1.93 | 4-NO₂ | —C₂H₅ | N | |
| 1.94 | 4-F | —CH₃ | CH | |
| 1.95 | 4-F | —CH₂CH₂OCH₃ | N | |
| 1.96 | 2,4-Di—Br | H | N | |
| 1.97 | 2-Cl, 4-Br | H | N | m.p. 226–233° C. (hydrochloride) |
| 1.98 | 2-Cl, 4-Br | —C(CH₃)₂—C₂H₅ | N | |
| 1.99 | 2,4-Di—Br | CH₃ | N | |
| 1.100 | 2-Cl, 4-F | CH₃ | N | m.p. 168–172° C. |
| 1.101 | " | C₂H₅ | N | m.p. 173–177° C. |
| 1.102 | " | C₂H₅ | CH | |
| 1.103 | " | C₃H₇—i | N | |
| 1.104 | " |  | N | |
| 1.105 | 2-Cl, 4-Br | 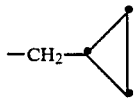 | N | |
| 1.106 | " | 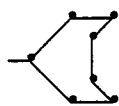 | N | |
| 1.107 | 2,4-Di—Cl | 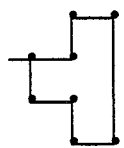 | N | |

TABLE 1-continued

Compounds of the formula

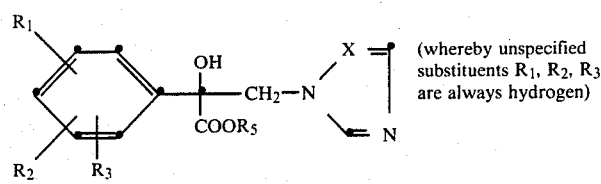 (whereby unspecified substituents $R_1$, $R_2$, $R_3$ are always hydrogen)

| Comp. No. | $R_1$, $R_2$, $R_3$ | $R_5$ | X | Physical data [m.p.] |
|---|---|---|---|---|
| 1.108 | " | (cyclopropyl) | N | |
| 1.109 | " | —CH$_2$—C$_6$H$_4$—Cl | N | |
| 1.110 | 2-Cl, 4-Br | —CH$_2$CH$_2$Cl | N | m.p. 113–116° C. |
| 1.111 | 2,4-Di—Br | C$_2$H$_5$ | N | m.p. 151–153° C. |
| 1.112 | 2-Cl, 4-Br | —CH$_2$-(thienyl) | N | |
| 1.113 | 4-F | C$_2$H$_5$ | N | |
| 1.114 | 2,6-Di—Cl | C$_2$H$_5$ | N | |
| 1.115 | 4-F | —C(CH$_3$)$_3$ | N | |
| 1.116 | 2,4-Di—Cl | —CH$_2$SCH$_3$ | N | 145–147° C. |
| 1.117 | 2,4-Di—Cl | —CH$_2$CH$_2$Cl | N | |
| 1.118 | " | —CH$_2$CO—CH$_3$ | N | |
| 1.119 | " | —CH$_2$SCH$_3$ | CH | |
| 1.120 | 2-Cl, 4-F | —CH$_2$SCH$_3$ | N | |
| 1.121 | " | —CH$_2$—COOC$_2$H$_5$ | N | |
| 1.122 | " | —CH$_2$—CO—C(CH$_3$)$_3$ | N | |
| 1.123 | " | —CH$_2$CH$_2$Cl | N | |
| 1.124 | " | —C$_6$H$_4$(CF$_3$)—4 | N | |
| 1.125 | 2-Cl, 4-Br | —CH$_2$CO—C$_6$H$_3$(Cl)(Cl) | N | |
| 1.126 | 2,4-Di—Cl | —CH$_2$CH$_2$F | N | |

TABLE 2

Compounds of the formula I with Ar = phenyl,
wherein n = 1 (acyl and oxalyl derivatives) and
R = COOR$_5$

| Comp. No. | $R_1$, $R_2$, $R_3$ | $R_4$ | $R_5$ | X | Physical data |
|---|---|---|---|---|---|
| 2.1 | H | —CH$_3$ | —CH$_3$ | N | |
| 2.2 | 2,4-Di-Cl | —CH$_3$ | —CH$_3$ | N | m.p. 143–144° C. |
| 2.3 | " | —CH$_3$ | —C$_2$H$_5$ | N | m.p. 149–151° C. |
| 2.4 | " | —CH$_3$ | —C$_3$H$_7$(i) | N | m.p. 144–150° C. |
| 2.5 | " | —CH$_3$ | —CH$_3$ | CH | m.p. 138–141° C. |
| 2.6 | " | —CH$_3$ | —C$_4$H$_9$(n) | N | oil |
| 2.7 | " | —CH$_3$ | —C$_3$H$_7$(n) | N | |
| 2.8 | " | —CH$_3$ | —C$_4$H$_9$(t) | N | |
| 2.9 | " | —CH$_3$ | —CH$_2$CH=CH$_2$ | N | m.p. 152–156° C. |
| 2.10 | " | —CH$_3$ | —CH$_2$CH$_2$OCH$_3$ | N | |
| 2.11 | " | —CH$_3$ | —CH$_2$CH$_2$Cl | N | |
| 2.12 | " | —CH$_3$ | —CH$_2$OCH$_3$ | N | |
| 2.13 | " | —CH$_3$ | —CH$_2$—C$_6$H$_5$ | N | |

TABLE 2-continued

Compounds of the formula I with Ar = phenyl, wherein n = 1 (acyl and oxalyl derivatives) and R = COOR$_5$

| Comp. No. | R$_1$, R$_2$, R$_3$ | R$_4$ | R$_5$ | Physical data | |
|---|---|---|---|---|---|
| 2.14 | " | —CH$_3$ | 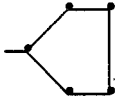 | N | |
| 2.15 | " | —CH$_3$ | 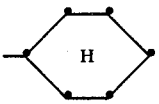 | N | |
| 2.16 | " | —CH$_3$ | —CH$_2$—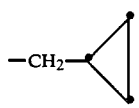 | N | |
| 2.17 | " | —CH$_3$ | —CH$_2$C≡CH | N | |
| 2.18 | " | —CH$_3$ | —C$_{12}$H$_{25}$(n) | N | |
| 2.19 | " | —CH$_3$ | —CH$_2$—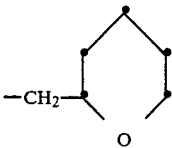 | N | |
| 2.20 | " | —CH$_3$ | —CH$_2$—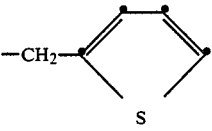 | N | |
| 2.21 | " | —CH$_3$ | —CH$_2$COOC$_2$H$_5$ | N | |
| 2.22 | " | —CH$_3$ | —CH(CH$_3$)COOCH$_3$ | N | |
| 2.23 | " | —C$_2$H$_5$ | —CH$_3$ | N | |
| 2.24 | " | —C$_2$H$_5$ | —C$_2$H$_5$ | N | |
| 2.25 | " | —C$_2$H$_5$ | —C$_2$H$_5$ | CH | |
| 2.26 | " | —C$_2$H$_5$ | —C$_3$H$_7$(n) | N | |
| 2.27 | " | —C$_2$H$_5$ | —C$_3$H$_7$(i) | N | |
| 2.28 | " | —C$_2$H$_5$ | —C$_4$H$_9$(n) | N | |
| 2.29 | " | —C$_2$H$_5$ | —CH$_2$CH=CH$_2$ | N | |
| 2.30 | " | —C$_2$H$_5$ | —CH$_2$CH$_2$OCH$_3$ | N | |
| 2.31 | " | —C$_2$H$_5$ | —CH$_2$OCH$_3$ | N | |
| 2.32 | " | —C$_2$H$_5$ | —C$_4$H$_9$(t) | N | |
| 2.33 | " | —CH$_2$OCH$_3$ | —CH$_3$ | N | |
| 2.34 | " | —CH$_2$OCH$_3$ | —CH$_3$ | CH | |
| 2.35 | " | —CH$_2$OCH$_3$ | —C$_2$H$_5$ | N | oil |
| 2.36 | " | —CH$_2$OCH$_3$ | —C$_3$H$_7$(n) | N | |
| 2.37 | " | —CH$_2$OCH$_3$ | —C$_3$H$_7$(i) | N | |
| 2.38 | " | —CH$_2$OCH$_3$ | —C$_4$H$_9$(n) | N | |
| 2.39 | " | —CH$_2$OCH$_3$ | —C$_4$H$_9$(t) | N | |
| 2.40 | " | —CH$_2$OCH$_3$ | —CH$_2$CH=CH$_2$ | N | |
| 2.41 | " | " | —CH$_2$CH$_2$OCH$_3$ | N | |
| 2.42 | " | —CCl=CCl$_2$ | —CH$_3$ | N | |
| 2.43 | " | " | —C$_2$H$_5$ | N | |
| 2.44 | " | —CH$_2$Cl | —CH$_3$ | N | |
| 2.45 | " | —CH$_2$Cl | —C$_2$H$_5$ | N | |
| 2.46 | " | 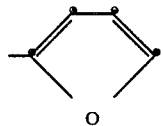 | —CH$_3$ | N | |
| 2.47 | " | 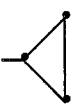 | —CH$_3$ | N | |

TABLE 2-continued

Compounds of the formula I with Ar = phenyl, wherein n = 1 (acyl and oxalyl derivatives) and R = COOR$_5$

| Comp. No. | R$_1$, R$_2$, R$_3$ | R$_4$ | R$_5$ | Physical data | |
|---|---|---|---|---|---|
| 2.48 | " | —C$_6$H$_3$Cl$_2$(3,4) | —C$_2$H$_5$ | N | |
| 2.49 | " | phenyl (H) | —C$_2$H$_5$ | N | oil |
| 2.50 | " | cyclopropyl | —CH$_3$ | CH | |
| 2.51 | " | —CH$_2$OC$_2$H$_5$ | —C$_4$H$_9$(n) | CH | |
| 2.52 | " | —CH$_2$—C$_6$H$_3$Cl$_2$(2,4) | —C$_2$H$_5$ | N | |
| 2.53 | " | —CH$_2$—C$_6$H$_3$Cl$_2$(2,4) | —CH$_3$ | N | |
| 2.54 | " | —CH$_2$OC$_2$H$_5$ | —C$_6$H$_4$Cl(4) | N | |
| 2.55 | " | oxetanyl | —CH$_3$ | N | oil |
| 2.56 | " | dioxolenyl | —C$_2$H$_5$ | CH | |
| 2.57 | " | 2,6-dichloropyridinyl | —C$_6$H$_4$—CH$_3$(4) | N | |
| 2.58 | " | —C$_{12}$H$_{25}$(n) | —CH$_3$ | N | |
| 2.59 | 4-CH$_3$ | —CCl=CCl$_2$ | —CH$_3$ | N | |
| 2.60 | 2-Cl | —CCl=CCl$_2$ | —C$_6$H$_4$Cl(4) | N | |
| 2.61 | 4-Cl | —CCl=CCl$_2$ | —CH$_3$ | CH | |
| 2.62 | 4-Br | —CCl=CCl$_2$ | —C$_2$H$_5$ | N | |
| 2.63 | 3-NO$_2$ | 4-bromophenyl | —CH$_3$ | N | |
| 2.64 | 4-Cl | —CH$_3$ | —C$_2$H$_5$ | N | oil |
| 2.65 | " | —C$_2$H$_5$ | —C$_2$H$_5$ | N | resin |
| 2.66 | 2-Cl, 4-Br | —CH$_3$ | —C$_2$H$_5$ | N | m.p. 85-87° C. |
| 2.67 | " | —CH$_3$ | —CH$_3$ | N | m.p. 146-148° C. |
| 2.68 | " | —CH$_3$ | —C$_3$H$_7$(i) | N | oil |
| 2.69 | " | —CH$_3$ | —C$_4$H$_9$(n) | N | |
| 2.70 | " | —CH$_3$ | —C$_4$H$_9$(t) | N | |
| 2.71 | " | —CH$_3$ | —C$_2$H$_5$ | CH | |
| 2.72 | " | —CH$_3$ | —CH$_2$CH$_2$OCH$_3$ | N | |
| 2.73 | " | —CH$_3$ | —CH$_2$CH$_2$Cl | N | |
| 2.74 | " | —CH$_3$ | —CH$_2$CH=CH$_2$ | N | |
| 2.75 | " | —CH$_3$ | —CH$_2$OCH$_3$ | N | |
| 2.76 | " | —CH$_3$ | —CH$_2$—C$_6$H$_5$ | N | |
| 2.77 | " | —CH$_3$ | —CH$_2$C≡CH | N | |

TABLE 2-continued

Compounds of the formula I with Ar = phenyl, wherein n = 1 (acyl and oxalyl derivatives) and R = COOR$_5$

| Comp. No. | R$_1$, R$_2$, R$_3$ | R$_4$ | R$_5$ | | Physical data |
|---|---|---|---|---|---|
| 2.78 | " | —CH$_3$ | 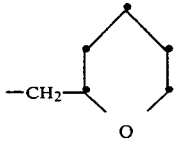 | N | |
| 2.79 | " | —CH$_3$ | 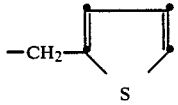 | N | |
| 2.80 | " | —C$_2$H$_5$ | —C$_2$H$_5$ | N | |
| 2.81 | " | —C$_2$H$_5$ | —CH$_3$ | N | |
| 2.82 | " | —CH$_2$OCH$_3$ | —C$_2$H$_5$ | N | |
| 2.83 | " | —CH$_2$Cl | —C$_2$H$_5$ | N | |
| 2.84 | " | —CCl=CCl$_2$ | C$_2$H$_5$ | N | oil |
| 2.85 | " | —CH$_2$OC$_2$H$_5$ | C$_6$H$_4$Cl(4) | N | |
| 2.86 | " | 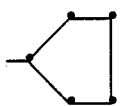 | CH$_3$ | N | |

| Comp. No. | R$_1$, R$_2$, R$_3$ | R$_4$ | R$_5$ | X | Physical data |
|---|---|---|---|---|---|
| 2.87 | " | —C$_6$H$_3$Cl$_2$(2,4) | C$_2$H$_5$ | N | |
| 2.88 | " | 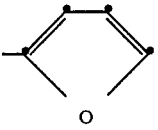 | C$_2$H$_5$ | N | |
| 2.89 | " | —CH$_3$ | 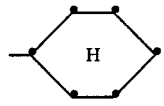 | N | |
| 2.90 | " | —CH$_3$ | 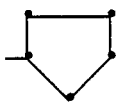 | N | |
| 2.91 | " | —CH$_3$ | —C$_6$H$_5$ | N | |
| 2.92 | 2-Cl, 4-F | —CH$_3$ | —CH$_3$ | N | m.p. 165–171° C. |
| 2.93 | " | —CH$_3$ | —CH$_3$ | CH | |
| 2.94 | " | —CH$_3$ | —C$_2$H$_5$ | N | |
| 2.95 | " | —CH$_2$OCH$_3$ | —C$_2$H$_5$ | N | |
| 2.96 | " | —CCl=CCl$_2$ | —C$_2$H$_5$ | N | |
| 2.97 | " | —CH$_3$ | —C$_3$H$_7$(i) | N | |
| 2.98 | " | —CH$_3$ | —C$_4$H$_9$(n) | N | |
| 2.99 | " | —CH$_3$ | —C$_4$H$_9$(t) | N | |
| 2.100 | " | —CH$_3$ | —CH$_2$—C$_6$H$_5$ | N | |
| 2.101 | " | —CH$_3$ | —CH$_2$CH=CH$_2$ | N | |
| 2.102 | 2,4-Di-Br | —CH$_3$ | —CH$_3$ | N | |
| 2.103 | " | —CH$_3$ | —C$_2$H$_5$ | N | resin |
| 2.104 | " | —CH$_3$ | —C$_3$H$_7$(i) | N | |
| 2.105 | " | —CH$_3$ | —C$_4$H$_9$(t) | N | |
| 2.106 | 2,3,4-Tri-Cl | —CH$_3$ | —CH$_3$ | N | |
| 2.107 | 3,4-Di-Cl | —CH$_3$ | —C$_2$H$_5$ | N | |
| 2.108 | 2,4-Di-Cl | —OCH$_3$ | —CH$_3$ | N | |
| 2.109 | " | —OC$_2$H$_5$ | —CH$_3$ | N | m.p. 98–100° C. |
| 2.110 | " | —OC$_2$H$_5$ | —C$_2$H$_5$ | N | resin |
| 2.111 | " | —OC$_2$H$_5$ | —C$_2$H$_5$ | CH | m.p. 165° C. (decomp.) |
| 2.112 | " | —OC$_2$H$_5$ | —C$_3$H$_7$(n) | N | |
| 2.113 | " | " | —C$_3$H$_7$(i) | N | |
| 2.114 | " | " | —C$_4$H$_9$(n) | N | |
| 2.115 | " | " | —C$_4$H$_9$(t) | N | |

TABLE 2-continued

Compounds of the formula I with Ar = phenyl, wherein n = 1 (acyl and oxalyl derivatives) and R = COOR$_5$

| Comp. No. | R$_1$, R$_2$, R$_3$ | R$_4$ | R$_5$ | Physical data | |
|---|---|---|---|---|---|
| 2.116 | " | " | —CH$_2$CH$_2$OCH$_3$ | N | |
| 2.117 | " | " | —CH$_2$CH$_2$Cl | N | |
| 2.118 | " | " | —CH$_2$OCH$_3$ | N | |
| 2.119 | " | " | —CH$_2$—C$_6$H$_5$ | N | |
| 2.120 | " | " | —C$_6$H$_5$ | N | |
| 2.121 | " | —O—CH$_2$—C$_6$H$_5$ | —C$_2$H$_5$ | N | |
| 2.122 | " | —O—C$_6$H$_5$ | —C$_2$H$_5$ | N | |
| 2.123 | " | —O—⟨H⟩ (cyclohexyl) | —C$_2$H$_5$ | N | |
| 2.124 | " | —OCH$_2$CH=CH$_2$ | —C$_2$H$_5$ | N | |
| 2.125 | " | —SC$_2$H$_5$ | —CH$_3$ | N | m.p. 85–87° C. |
| 2.126 | " | —SC$_2$H$_5$ | —C$_2$H$_5$ | N | |
| 2.127 | " | —SC$_2$H$_5$ | —C$_2$H$_5$ | CH | |
| 2.128 | " | —S—CH$_2$—C$_6$H$_5$ | —C$_2$H$_5$ | N | |
| 2.129 | " | —SCH$_3$ | —CH$_3$ | N | |
| 2.130 | " | —SC$_3$H$_7$(i) | —C$_2$H$_5$ | N | |
| 2.131 | 2-Cl, 4-Br | —OCH$_3$ | —CH$_3$ | N | |
| 2.132 | " | —OC$_2$H$_5$ | —C$_2$H$_5$ | N | oil |
| 2.133 | " | —OC$_2$H$_5$ | —C$_2$H$_5$ | CH | |
| 2.134 | " | —O—⟨H⟩ (cyclohexyl) | —C$_2$H$_5$ | N | |
| 2.135 | " | —O—C$_6$H$_5$ | —C$_2$H$_5$ | N | |
| 2.136 | " | —O—CH$_2$—C$_6$H$_5$ | —C$_2$H$_5$ | N | |
| 2.137 | " | —OCH$_2$CH=CH$_2$ | —C$_2$H$_5$ | N | |
| 2.138 | " | —OC$_3$H$_7$(n) | —C$_2$H$_5$ | N | |
| 2.139 | " | —OC$_4$H$_9$(n) | —C$_2$H$_5$ | N | |
| 2.140 | " | —OC$_2$H$_5$ | —C$_3$H$_7$(n) | N | |
| 2.141 | " | —OC$_2$H$_5$ | —C$_3$H$_7$(i) | N | oil |
| 2.142 | " | —OC$_2$H$_5$ | —C$_4$H$_9$(n) | N | |
| 2.143 | " | —OC$_2$H$_5$ | —CH$_2$CH=CH$_2$ | N | |
| 2.144 | " | —OC$_2$H$_5$ | —CH$_2$CH$_2$OCH$_3$ | N | |
| 2.145 | " | " | —CH$_2$CH$_2$Cl | N | |
| 2.146 | " | " | —CH$_2$—C$_6$H$_5$ | N | |
| 2.147 | " | " | —CH$_2$OCH$_3$ | N | |
| 2.148 | " | —SCH$_3$ | —C$_2$H$_5$ | N | |
| 2.149 | " | —SC$_2$H$_5$ | —C$_2$H$_5$ | N | yellow oil |
| 2.150 | " | —SCH$_2$—C$_6$H$_5$ | —C$_2$H$_5$ | N | |
| 2.151 | " | —SC$_2$H$_5$ | —C$_3$H$_7$(n) | N | |
| 2.152 | " | —SC$_2$H$_5$ | —C$_4$H$_9$(t) | N | |
| 2.153 | " | —SC$_2$H$_5$ | —CH$_2$CH=CH$_2$ | N | |
| 2.154 | 2,4-Di-Br | —SC$_2$H$_5$ | —C$_2$H$_5$ | N | resin |
| 2.155 | " | —OC$_2$H$_5$ | —C$_2$H$_5$ | N | resin |
| 2.156 | " | —OCH$_3$ | —CH$_3$ | N | |
| 2.157 | 2-Cl, 4-F | —OC$_2$H$_5$ | —CH$_3$ | N | viscous |
| 2.158 | " | —OC$_2$H$_5$ | —C$_2$H$_5$ | N | |
| 2.159 | " | —OC$_2$H$_5$ | —C$_3$H$_7$(i) | N | |
| 2.160 | " | —OC$_2$H$_5$ | —C$_4$H$_9$(t) | N | |
| 2.161 | " | —SC$_2$H$_5$ | —C$_2$H$_5$ | N | resin |
| 2.162 | " | —SCH$_3$ | —CH$_3$ | N | |
| 2.163 | " | —SCH$_2$—C$_6$H$_5$ | —C$_2$H$_5$ | N | |
| 2.164 | " | —OCH$_3$ | —CH$_3$ | N | |
| 2.165 | " | —OCH$_2$—C$_6$H$_5$ | —C$_2$H$_5$ | N | |
| 2.166 | " | —OC$_2$H$_5$ | —CH$_2$CH=CH$_2$ | N | |
| 2.167 | " | —OC$_2$H$_5$ | —C$_2$H$_5$ | CH | |
| 2.168 | 3,4-Di-Cl | —OC$_2$H$_5$ | —C$_2$H | N | |
| 2.169 | " | —SC$_2$H$_5$ | —C$_2$H$_5$ | N | |
| 2.170 | 2-Cl, 4-Br | —OC$_2$H$_5$ | —CH$_3$ | N | resin |
| 2.171 | " | —COOCH$_3$ | —C$_2$H$_5$ | N | |
| 2.172 | " | —COOC$_2$H$_5$ | —C$_2$H$_5$ | N | |
| 2.173 | 2,4-Di-Cl | —COOCH$_3$ | —CH$_3$ | N | |
| 2.174 | " | —COOCH$_3$ | —CH$_3$ | CH | |
| 2.175 | " | —COOC$_2$H$_5$ | —C$_2$H$_5$ | N | |
| 2.176 | " | —COOC$_2$H$_5$ | —CH$_3$ | N | |
| 2.177 | " | —N(CH$_3$)$_2$ | —CH$_3$ | N | |
| 2.178 | " | —N(C$_2$H$_5$)$_2$ | —C$_2$H$_5$ | N | |
| 2.179 | " | —1-imidazolyl | —C$_2$H$_5$ | N | |

TABLE 2-continued

Compounds of the formula I with Ar = phenyl, wherein n = 1 (acyl and oxalyl derivatives) and R = COOR$_5$

| Comp. No. | R$_1$, R$_2$, R$_3$ | R$_4$ | R$_5$ | X | Physical data |
|---|---|---|---|---|---|
| 2.180 | " | —N(C$_4$H$_9$sec)$_2$ | —C$_2$H$_5$ | N | |
| 2.181 | 2-Cl, 4-Br | —N(CH$_3$)$_2$ | —C$_2$H$_5$ | N | m.p. 45–66° |
| 2.182 | " | —N(C$_2$H$_5$)$_2$ | —C$_2$H$_5$ | N | |
| 2.183 | " | —N(C$_4$H$_9$sec)$_2$ | —C$_2$H$_5$ | N | |
| 2.184 | " | 1-(1,2,4-triazolyl) | —C$_2$H$_5$ | N | |
| 2.185 | 2,4-Di-Cl | —N(CH$_3$)$_2$ | —C$_3$H$_7$(i) | N | |
| 2.186 | " | —N(CH$_3$)$_2$ | —C$_4$H$_9$(n) | N | |
| 2.187 | " | —N(C$_2$H$_5$)$_2$ | —CH$_2$C—C$_6$H$_5$ | N | |
| 2.188 | " | —CH$_2$—COOC$_2$H$_5$ | —C$_2$H$_5$ | N | |
| 2.189 | " | —CH(CH$_3$)COOC$_2$H$_5$ | —CH$_3$ | N | |
| 2.190 | " | —CH(CH$_3$)COOCH$_3$ | —CH$_3$ | N | |
| 2.191 | 2-Cl, 4-Br | —CH$_2$—COOC$_2$H$_5$ | —C$_2$H$_5$ | N | |
| 2.192 | " | —CH(CH$_3$)COOCH$_3$ | —C$_2$H$_5$ | N | |
| 2.193 | 4-Cl | —OC$_2$H$_5$ | —C$_2$H$_5$ | N | oil |

TABLE 3

Compounds of the formula I with Ar = phenyl, wherein n = nought

| Comp. No. | R$_1$, R$_2$, R$_3$ | R$_4$ | R$_5$ | X | Physical data |
|---|---|---|---|---|---|
| 3.1 | 2,4-Di-Cl | —CH$_2$CH=CH$_2$ | —CH$_3$ | N | |
| 3.2 | " | —CH$_3$ | —CH$_3$ | N | |
| 3.3 | " | —C$_2$H$_5$ | —C$_2$H$_5$ | N | resin |
| 3.4 | " | —CH$_2$CH=CH$_2$ | —C$_2$H$_5$ | N | oil |
| 3.5 | " | —CH$_2$CH=CH$_2$ | —C$_2$H$_5$ | CH | |
| 3.6 | " | —CH$_2$—C$_6$H$_5$ | —C$_2$H$_5$ | N | |
| 3.7 | " | —CH$_2$COC(CH$_3$)$_3$ | —C$_2$H$_5$ | N | |
| 3.8 | " | 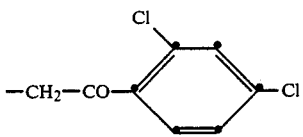 —CH$_2$—CO—(2-Cl,4-Cl-phenyl) | —CH$_3$— | N | |
| 3.9 | " | —CH$_2$OCH$_3$ | —C$_2$H$_5$ | N | |
| 3.10 | " | —CH$_2$SCH$_3$ | —C$_2$H$_5$ | N | |
| 3.11 | " | —C(CH$_3$)COOCH$_3$ | C$_2$H$_5$ | N | |
| 3.12 | " | —CH$_3$ | —C$_4$H$_9$(n) | N | oil |
| 3.13 | " | —C$_2$H$_5$ | —C$_4$H$_9$(i) | N | |
| 3.14 | " | —C$_4$H$_9$(n) | —C$_4$H$_9$(n) | N | |
| 3.15 | " | —C$_3$H$_7$(n) | —C$_3$H$_7$(n) | CH | |
| 3.16 | " | —CH$_2$—C$_6$H$_5$ | —CH$_2$—C$_6$H$_5$ | N | |
| 3.17 | " | —CH$_2$CH=CH$_2$ | —CH$_2$CH=CH$_2$ | N | |
| 3.18 | " | —CH$_2$CH=CH$_2$ | —CH$_2$CH=CH$_2$ | CH | |
| 3.19 | " | —C$_4$H$_9$(n) | C$_6$H$_3$Cl$_2$(2,4) | N | |
| 3.20 | " | —C$_2$H$_5$ | —C(CH$_3$)$_3$ | N | |
| 3.21 | " | —CH$_2$CH$_2$CN | —CH$_3$ | N | |
| 3.22 | " | —CH$_2$CH$_2$COOC$_2$H$_5$ | —CH$_3$ | N | |
| 3.23 | " | —CH$_2$COC$_6$H$_3$Cl$_2$(2,4) | —CH$_3$ | CH | |
| 3.24 | " | —CH$_2$COCH$_3$ | —C$_2$H$_5$ | N | |
| 3.25 | " | —C$_3$H$_7$(n) | —CH$_3$ | N | resin |
| 3.26 | " | —C$_4$H$_9$(n) | —CH$_2$CH=CH$_2$ | N | resin |
| 3.27 | " | —C$_{12}$H$_{25}$(n) | —CH$_3$ | N | resin |
| 3.28 | 4-Cl | —C$_3$H$_7$ | —C$_3$H$_7$(n) | N | |
| 3.29 | " | —CH$_2$CH=CH$_2$ | —CH$_3$ | N | |
| 3.30 | " | —CH$_2$COC$_6$H$_4$Cl(4) | —C$_6$H$_4$Cl(4) | N | |
| 3.31 | 2,3,4-Tri-Cl | —CH$_2$CH=CH$_2$ | —CH$_2$CH=CH$_2$ | N | |
| 3.32 | 4-Br | —CH$_3$ | —CH$_3$ | N | m.p. 80–92° C. |
| 3.33 | 2-CH$_3$ | —CH$_3$ | —CH$_3$ | N | |
| 3.34 | 2-Cl, 4-Br | —CH$_3$ | —CH$_3$ | N | |
| 3.35 | " | —CH$_2$CH=CH$_2$ | —C$_2$H$_5$ | N | |
| 3.36 | " | —CH$_2$COC$_6$H$_4$Cl(4) | —C$_6$H$_4$Cl(4) | N | |
| 3.37 | " | —CH$_2$—C$_6$H$_5$ | —CH$_2$C$_6$H$_5$ | N | |
| 3.38 | " | —CH$_2$COC(CH$_3$)$_3$ | —C$_2$H$_5$ | N | |
| 3.39 | " | —CH$_2$CH=CH$_2$ | —C$_2$H$_5$ | CH | |
| 3.40 | 2-Cl, 4-F | —CH$_2$CH=CH$_2$ | —C$_2$H$_5$ | N | |
| 3.41 | " | —CH$_3$ | —CH$_3$ | N | |
| 3.42 | 2-Br, 4-Br | —CH$_2$CH=CH$_2$ | —C$_2$H$_5$ | N | |
| 3.43 | 2,4-Di-Cl | —CH$_2$CH=CH$_2$ | —C$_4$H$_9$(n) | N | oil |
| 3.44 | 4-Br | —CH$_3$ | —C$_2$H$_5$ | N | m.p. 65–67° C. |
| 3.45 | 2-Cl, 4-Cl | —CH$_2$COOC$_2$H$_5$ | —CH$_3$ | N | |
| 3.46 | " | —C(CH$_3$)COOCH$_3$ | —CH$_3$ | N | |
| 3.47 | 2-Cl, 4-Br | —CH$_2$COOC$_2$H$_5$ | —C$_2$H$_5$ | N | |

TABLE 3-continued

Compounds of the formula I with Ar = phenyl, wherein n = nought

| Comp. No. | $R_1, R_2, R_3$ | $R_4$ | $R_5$ | X | Physical data |
|---|---|---|---|---|---|
| 3.48 | " | $-C(CH_3)COOCH_3$ | $-C_2H_5$ | N | |

TABLE 4

Compounds of the formula I wherein Ar = phenyl, and R = $-COSR_6$

| Comp. No. | $R_1, R_2, R_3$ | $R_4$ | $R_6$ | X | n | Physical data |
|---|---|---|---|---|---|---|
| 4.1 | H | H | $-C_2H_5$ | N | 0 | |
| 4.2 | 2,4-Di-Cl | H | $-CH_3$ | N | 0 | |
| 4.3 | " | H | $-C_2H_5$ | N | 0 | m.p. 180–182° C. |
| 4.4 | " | H | $-C_2H_5$ | CH | 0 | |
| 4.5 | " | H | $-C_3H_7(n)$ | N | 0 | |
| 4.6 | " | H | $-CH_2-C_6H_5$ | N | 0 | m.p. 171–173° |
| 4.7 | " | H | $-C_6H_5$ | N | 0 | m.p. 164–166° |
| 4.8 | " | $-CH_2CH=CH_2$ | $-C_2H_5$ | N | 0 | |
| 4.9 | " | $-CH_2-C_6H_5$ | $-C_2H_5$ | N | 0 | |
| 4.10 | " | $-CH_3$ | $-C_2H_5$ | N | 1 | |
| 4.11 | " | $-CH_3$ | $-C_2H_5$ | CH | 1 | |
| 4.12 | " | $-CH_2OCH_3$ | $-C_2H_5$ | N | 1 | |
| 4.13 | " | $-C_2H_5$ | $-C_2H_5$ | N | 1 | |
| 4.14 | 2-Cl, 4-Br | H | $-CH_3$ | N | 0 | |
| 4.15 | " | H | $-C_2H_5$ | N | 0 | |
| 4.16 | " | H | $-CH_2-C_6H_5$ | N | 0 | |
| 4.17 | " | H | $-C_6H_5$ | N | 0 | |
| 4.18 | " | H | $-C_2H_5$ | N | 0 | |
| 4.19 | " | $-CH_2CH=CH_2$ | $-C_2H_5$ | N | 0 | |
| 4.20 | " | $-CH_3$ | $-C_2H_5$ | N | 1 | |
| 4.21 | " | $-C_2H_5$ | $-C_2H_5$ | N | 1 | |
| 4.22 | " | $-CH_2OCH_3$ | $-C_2H_5$ | N | 1 | |
| 4.23 | 4-Cl | H | $-C_2H_5$ | N | 0 | |
| 4.24 | 2-Cl, 4-F | H | $-C_2H_5$ | N | 0 | |
| 4.25 | " | H | $-CH_3$ | N | 0 | |
| 4.26 | " | H | $-C_2H_5$ | CH | 0 | |
| 4.27 | " | $-CH_3$ | $-C_2H_5$ | N | 1 | |
| 4.28 | 2,4-Di-Br | H | $-C_2H_5$ | N | 0 | |
| 4.29 | " | $-CH_3$ | $-C_2H_5$ | N | 1 | |
| 4.30 | " | $-OC_2H_5$ | $-C_2H_5$ | N | 1 | |
| 4.31 | " | $-SC_2H_5$ | $-C_2H_5$ | N | 1 | |
| 4.32 | 2,4-Di-Cl | H | $-CH_2CH=CH_2$ | N | 0 | |
| 4.33 | " | $-CH_3$ | $-CH_2CH=CH_2$ | N | 1 | |
| 4.34 | " | $-OCH_3$ | $-CH_3$ | N | 1 | |
| 4.35 | " | $-OC_2H_5$ | $-C_2H_5$ | N | 1 | |
| 4.36 | " | $-OCH_2-C_6H_5$ | $-C_2H_5$ | N | 1 | |
| 4.37 | " | $-O-C_6H_5$ | $-C_2H_5$ | N | 1 | |
| 4.38 | " | 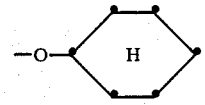 | $-C_2H_5$ | N | 1 | |
| 4.39 | " | $-SCH_3$ | $-CH_3$ | N | 1 | |
| 4.40 | " | $-SC_2H_5$ | $-C_2H_5$ | N | 1 | oil |
| 4.41 | " | $-SCH_2-C_6H_5$ | $-CH_2-C_6H_5$ | N | 1 | |
| 4.42 | 2-Cl, 4-F | $-OC_2H_5$ | $-C_2H_5$ | N | 1 | |
| 4.43 | " | $-OCH_3$ | $-CH_3$ | N | 1 | |
| 4.44 | " | $-OCH_3$ | $-CH_3$ | N | 1 | |
| 4.45 | " | $-SC_2H_5$ | $-C_2H_5$ | N | 1 | |
| 4.46 | 2-Cl, 4-Cl | $-OCH_3$ | $-CH_3$ | N | 2 | |
| 4.47 | " | $-OC_2H_5$ | $-CH_3$ | N | 2 | |
| 4.48 | " | $-OC_2H_5$ | $-C_2H_5$ | N | 2 | |
| 4.49 | 2-Cl, 4-Br | $-OCH_3$ | $-C_2H_5$ | N | 2 | |
| 4.50 | " | $-OC_2H_5$ | $-C_2H_5$ | N | 2 | |
| 4.51 | " | $-N(CH_3)_2$ | $-C_2H_5$ | N | 1 | |
| 4.52 | " | $-N(C_2H_5)_2$ | $-C_2H_5$ | N | 1 | |
| 4.53 | 2-Cl, 4-Cl | $-N(CH_3)_2$ | $-CH_3$ | N | 1 | |
| 4.54 | " | $-N(C_2H_5)_2$ | $-CH_3$ | N | 1 | |
| 4.55 | " | $-N(C_4H_9sec)_2$ | $-CH_3$ | N | 1 | |
| 4.56 | " | 1-(1,2,4-triazolyl) | $-CH_3$ | N | 1 | |
| 4.57 | " | $-$1-imidazolyl | $-CH_3$ | N | 1 | |
| 4.58 | " | $-N(CH_3)_2$ | $-C_2H_5$ | N | 1 | |
| 4.59 | " | $-CH_2COOC_2H_5$ | $-C_2H_5$ | N | 0 | |
| 4.60 | " | $-CH_2COOC_2H_5$ | $-C_2H_5$ | N | 1 | |
| 4.61 | " | $-CH(CH_3)COOCH_3$ | $-C_2H_5$ | N | 0 | |
| 4.62 | " | $-CH(CH_3)COOCH_3$ | $-C_2H_5$ | N | 1 | |
| 4.63 | 2-Cl, 4-Br | $-CH_2COOC_2H_5$ | $-C_2H_5$ | N | 0 | resin |

TABLE 4-continued

Compounds of the formula I wherein Ar = phenyl, and R = —COSR$_6$

| Comp. No. | R$_1$, R$_2$, R$_3$ | R$_4$ | R$_6$ | X | n | Physical data |
|---|---|---|---|---|---|---|
| 4.64 | " | —CH$_2$COOC$_2$H$_5$ | —C$_2$H$_5$ | N | 1 | |
| 4.65 | " | —CH(CH$_3$)COOCH$_3$ | —C$_2$H$_5$ | N | 0 | |
| 4.66 | " | —CH(CH$_3$)COOCH$_3$ | —C$_2$H$_5$ | N | 1 | |

TABLE 5

Compounds of the formula I wherein Ar = phenyl, and R = —CON$\begin{subarray}{l}R_7\\R_8\end{subarray}$

| Comp. No. | R$_1$, R$_2$, R$_3$ | R$_4$ | —N$\begin{subarray}{l}R_7\\R_8\end{subarray}$ | X | n | Physical data |
|---|---|---|---|---|---|---|
| 5.1 | 2,4-Di-Cl | H | —NH$_2$ | N | 0 | |
| 5.2 | " | H | —NHCH$_3$ | N | 0 | m.p. 157° C. |
| 5.3 | " | H | —NHC$_2$H$_5$ | N | 0 | |
| 5.4 | " | H | —NHC$_2$H$_5$ | CH | 0 | |
| 5.5 | " | H | —NH—C$_6$H$_5$ | N | 0 | |
| 5.6 | " | H | —NH—CH$_2$—C$_6$H$_5$ | N | 0 | m.p. 164–166° C. |
| 5.7 | " | H | —NHN(CH$_3$)$_2$ | N | 0 | |
| 5.8 | " | H | —NHN(CH$_3$)$_2$ | N | 0 | |
| 5.9 | " | H | —NHNH—C$_6$H$_5$ | N | 0 | |
| 5.10 | " | H | —N(CH$_3$)$_2$ | N | 0 | |
| 5.11 | " | H | —N(C$_2$H$_5$)$_2$ | N | 0 | |
| 5.12 | " | H | —NH—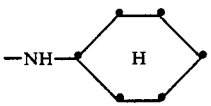H | N | 0 | |
| 5.13 | " | H | —NHCH$_3$ | CH | 0 | |
| 5.14 | " | —CH$_3$ | —NHCH$_3$ | N | 1 | |
| 5.15 | " | —C$_2$H$_5$ | —NHC$_2$H$_5$ | N | 1 | |
| 5.16 | " | —CH$_2$CH=CH$_2$ | —NHC$_2$H$_5$ | N | 0 | |
| 5.17 | 2-Cl, 4-Br | H | —NH$_2$ | N | 0 | |
| 5.18 | " | H | —NHCH$_3$ | N | 0 | |
| 5.19 | " | H | —NHC$_2$H$_5$ | N | 0 | |
| 5.20 | " | H | —NHCH$_2$—C$_6$H$_5$ | N | 0 | |
| 5.21 | " | H | —NHNH$_2$ | N | 0 | |
| 5.22 | " | H | —NHN(CH$_3$)$_2$ | N | 0 | m.p. 172–178° C. |
| 5.23 | " | H | —NHNH—C$_6$H$_5$ | N | 0 | |
| 5.24 | " | —CH$_2$CH=CH$_2$ | —NHC$_2$H$_5$ | N | 0 | |
| 5.25 | " | —CH$_3$ | —NHC$_2$H$_5$ | N | 1 | |
| 5.26 | 2-Cl, 4-F | H | —NHCH$_3$ | N | 0 | |
| 5.27 | " | H | —NHCH$_2$—C$_6$H$_5$ | N | 0 | |
| 5.28 | " | —CH$_3$ | —NHC$_2$H$_5$ | N | 0 | |
| 5.29 | " | —OC$_2$H$_5$ | —NHC$_2$H$_5$ | N | 1 | |
| 5.30 | " | —SC$_2$H$_5$ | —NHC$_2$H$_5$ | N | 1 | |
| 5.31 | 2,4-Di-Cl | —OCH$_3$ | —NHCH$_3$ | N | 1 | |
| 5.32 | " | —OC$_2$H$_5$ | —NHC$_2$H$_5$ | N | 1 | |
| 5.33 | " | —O—C$_6$H$_5$ | —NHC$_2$H$_5$ | N | 1 | |
| 5.34 | " | —OCH$_2$—C$_6$H$_5$ | —NHCH$_2$—C$_6$H$_5$ | N | 1 | |
| 5.35 | " | —OC$_2$H$_5$ | —NHN(CH$_3$)$_2$ | N | 1 | |
| 5.36 | " | —SC$_2$H$_5$ | —NHC$_2$H$_5$ | N | 1 | |
| 5.37 | 2-Cl, 4-Br | —OC$_2$H$_5$ | —NHC$_2$H$_5$ | N | 1 | |
| 5.38 | " | —SC$_2$H$_5$ | —NHC$_2$H$_5$ | N | 1 | |
| 5.39 | " | —OC$_2$H$_5$ | —NHCH$_3$ | N | 1 | |
| 5.40 | 2-Cl, 4-Cl | H | —N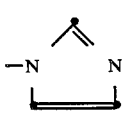N | N | 0 | m.p. 243–245° C. |
| 5.41 | " | —CH$_2$CH=CH$_2$ | " | N | 0 | |
| 5.42 | " | —CH$_3$ | " | N | 1 | |
| 5.43 | " | —OC$_2$H$_5$ | " | N | 1 | |
| 5.44 | 2-Cl, 4-Br | H | " | N | 0 | |
| 5.45 | " | —CH$_2$—C$_6$H$_5$ | " | N | 0 | |
| 5.46 | " | —CH$_3$ | " | N | 1 | |

TABLE 5-continued

Compounds of the formula I wherein Ar = phenyl, and R = $-CON\begin{subarray}{l}R_7\\R_8\end{subarray}$

| Comp. No. | $R_1, R_2, R_3$ | $R_4$ | $-N\begin{subarray}{l}R_7\\R_8\end{subarray}$ | X | n | Physical data |
|---|---|---|---|---|---|---|
| 5.47 | " | $-OC_2H_5$ | (1,2,4-triazol-1-yl) | N | 1 | |
| 5.48 | 2-Cl, 4-Cl | H | " | N | 0 | |
| 5.49 | 2-Cl, 4-Cl | H | (pyrazol-1-yl) | N | 0 | |
| 5.50 | " | $-OCH_3$ | $-NHCH_3$ | N | 2 | |
| 5.51 | " | $-OC_2H_5$ | $-NHC_2H_5$ | N | 2 | |
| 5.52 | " | $-N(CH_3)_2$ | $-NHCH_3$ | N | 1 | |
| 5.53 | " | $-N(CH_3)_2$ | $-NHC_2H_5$ | N | 1 | |
| 5.54 | " | $-N(C_2H_5)_2$ | $-NHC_2H_5$ | N | 1 | |
| 5.55 | " | $-N(C_4H_9sec)_2$ | $-NHCH_3$ | N | 1 | |
| 5.56 | " | (imidazol-1-yl) | $-NHCH_3$ | N | 1 | |
| 5.57 | " | 1-(1,2,4-triazolyl) | $-NHCH_3$ | N | 1 | |
| 5.58 | " | $-CH_2COOC_2H_5$ | $-NHC_2H_5$ | N | 0 | |
| 5.59 | " | $-CH_2COOC_2H_5$ | $-NHC_2H_5$ | N | 1 | |
| 5.60 | " | $-CH(CH_3)COOCH_3$ | $-NHC_2H_5$ | N | 0 | |
| 5.61 | " | $-CH(CH_3COOCH_3$ | $-NHC_2H_5$ | N | 1 | |
| 5.62 | 2-Cl, 4-Br | $-CH(CH_3)COOCH_3$ | $-NHCH_3$ | N | 0 | |
| 5.63 | " | $-CH(CH_3)COOCH_3$ | $-NHCH_3$ | N | 1 | |
| 5.64 | 4-Cl | H | $-N(CH_3)_2$ | N | 0 | m.p. 242-243° C. |
| 5.65 | 4-Br | H | $-N(CH_3)_2$ | N | 0 | m.p. 164-165° C. |

TABLE 6

Azolium salts of the formula

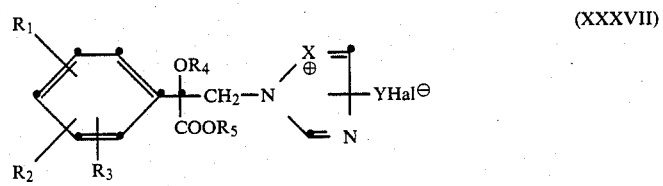

(XXXVII)

(whereby unspecified substituents $R_1, R_2, R_3$ are always hydrogen)

| Comp. No. | $R_1, R_2, R_3$ | $R_4$ | $R_5$ | X | Y Hal | Physical constants |
|---|---|---|---|---|---|---|
| 6.1 | 4-Br | H | $CH_3$ | N | $CH_3J$ | m.p. 150-157° C. (decomp.) |
| 6.2 | 2,4-Di-Cl | H | $CH_3$ | N | $CH_3J$ | |
| 6.3 | 4-Cl | $CH_3$ | $CH_3$ | N | $CH_3J$ | m.p. 88-96° C. |
| 6.4 | 4-Br | $CH_3$ | $CH_3$ | N | $CH_3J$ | |
| 6.5 | 2,4-Di-Cl | H | $CH_3$ | N | $BrCH_2COCH_3$ | |
| 6.6 | 2,4-Di-Cl | H | $CH_3$ | N | $ClCH_2C_6H_5$ | |
| 6.7 | 4-Br | H | $CH_3$ | N | $BrCH_2COC_6H_5$ | |
| 6.8 | 4-Cl | $CH_3$ | $CH_3$ | N | $ClCH_2CH_2SO_2CH_3$ | |
| 6.9 | 4-Cl | H | $CH_3$ | N | $BrCH(C_6H_5)_2$ | |
| 6.10 | 2,4-Di-Cl | H | $CH_3$ | N | $BrCH(CH_3)COOCH_3$ | |
| 6.11 | 2,4-Di-Cl | H | $CH_3$ | N | $BrCH_2COC_6H_3Cl_2(2,4)$ | |
| 6.12 | 2-Cl, 4-Br | H | $C_2H_5$ | N | $BrCH_2COC_6H_3Cl_2(2,4)$ | m.p. °C. 173-176 |

TABLE 6-continued

Azolium salts of the formula

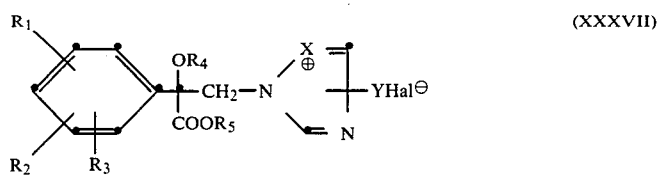
(XXXVII)

(whereby unspecified substituents $R_1$, $R_2$, $R_3$ are always hydrogen)

| Comp. No. | $R_1, R_2, R_3$ | $R_4$ | $R_5$ | X | Y Hal | Physical constants |
|---|---|---|---|---|---|---|
| 6.13 | 4-Br | $C_2H_5$ | $C_2H_5$ | N | $JC_4H_9$—n | |
| 6.14 | 4-Cl | $CH_3$ | $CH_3$ | N | $ClCH_2C_6H_5Cl(4)$ | |
| 6.15 | 2-Cl, 4-Br | H | $CH_3$ | N | $ClCH_2CN$ | |
| 6.16 | 2,3,4-Tri-Cl | H | $CH_3$ | N | $JC_3H_7$—n | |
| 6.17 | 4-Br | H | $CH_3$ | CH | $CH_3J$ | |
| 6.18 | 2,4-Di-Cl | H | $CH_3$ | N | $ClCH_2SCH_3$ | |
| 6.19 | 2,4-Di-Cl | $CH_3$ | $CH_3$ | N | $JCH_2CH_3$ | |
| 6.20 | 2,4-Di-Cl | H | $CH_3$ | CH | $JCH_2CH_3$ | |
| 6.21 | 2,4-Di-Cl | $CH_3$ | $CH_3$ | CH | $JCH_2CH_3$ | m.p. |
| 6.22 | 2-Cl, 4-Br | H | $C_2H_5$ | N | $\frac{1}{2}CuCl_2$ | 171–177° C. |

TABLE 7

Compounds of the formula

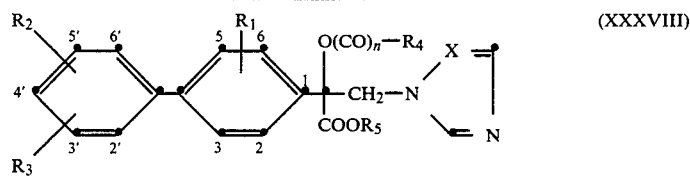
(XXXVIII)

| Comp. No. | $R_1$ | $R_2$ | $R_3$ | n | $R_4$ | $R_5$ | X | Physic. const. |
|---|---|---|---|---|---|---|---|---|
| 7.1 | H | H | H | 0 | $CH_3$ | $CH_3$ | N | m.p. |
| 7.2 | H | H | H | 0 | H | H | N | >200° C. |
| 7.3 | H | H | H | 0 | H | $CH_3$ | N | >182° C. |
| 7.4 | H | H | H | 0 | H | $CH_3$ | CH | |
| 7.5 | H | H | H | 0 | H | $C_2H_5$ | N | |
| 7.6 | H | H | H | 0 | H | $C_4H_9$—n | N | |
| 7.7 | H | 4'-Cl | H | 0 | H | $CH_3$ | N | |
| 7.8 | H | 4'-Br | H | 0 | H | $C_2H_5$ | N | |
| 7.9 | 2-OCH$_3$ | H | H | 0 | $CH_3$ | $C_3H_7$—n | N | |
| 7.10 | H | 2'-OCH$_3$ | 3'-Cl | 0 | H | $C_2H_5$ | N | |
| 7.11 | H | 4'-CH$_3$ | H | 0 | H | $CH_3$ | N | |
| 7.12 | H | 4'-CH$_3$ | H | 0 | $C_2H_5$ | $CH_3$ | CH | |
| 7.13 | H | 4'-Cl | H | 1 | $CH_3$ | $CH_3$ | N | |
| 7.14 | H | 4'-Cl | H | 1 | $CH_2CH=CH_2$ | $CH_3$ | N | |
| 7.15 | H | 4'-Cl | H | 1 | $CH_2CH_2CN$ | $CH_3$ | N | |
| 7.16 | H | 4'-Cl | H | 1 | $CCl=CCl_2$ | $CH_3$ | N | |
| 7.17 | H | 4'-Cl | H | 1 | 2-Tetrahydrofuryl | $C_2H_5$ | N | |
| 7.18 | H | 4'-Br | H | 1 | 2-Tetrahydrofuryl | $CH_3$ | CH | |
| 7.19 | H | 4'-Br | H | 0 | H | H | N | |
| 7.20 | H | H | H | 0 | H | $C_6H_3Cl_2(2,4)$ | N | |
| 7.21 | H | 4'-Cl | H | 1 | $CH_3$ | $C_6H_3Cl_2(2,4)$ | N | |
| 7.22 | H | 4'-Cl | H | 1 | Cyclopropyl | $C_6H_4Cl(4)$ | N | m.p. |
| 7.23 | 2-Cl | H | H | 0 | H | $CH_3$ | N | 174–182° C. |

TABLE 8

Compounds of the formula

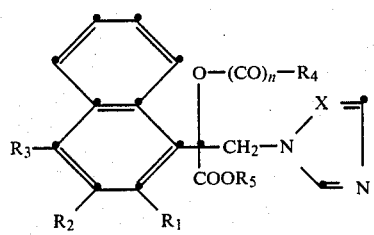
(XXXIX)

| Comp. No. | R₁ | R₂ | R₃ | n | R₄ | R₅ | X | Physical constants |
|---|---|---|---|---|---|---|---|---|
| 8.1 | H | H | H | 0 | H | H | N | |
| 8.2 | H | H | H | 0 | H | H | CH | |
| 8.3 | H | H | H | 0 | CH₃ | CH₃ | N | |
| 8.4 | H | H | H | 0 | CH₃ | CH₃ | CH | |
| 8.5 | H | H | H | 0 | H | CH₃ | N | m.p >200° C. (decomp.) |
| 8.6 | H | H | H | 0 | H | CH₃ | CH | |
| 8.7 | H | H | H | 0 | H | C₂H₅ | N | |
| 8.8 | H | H | H | 1 | CH₃ | CH₃ | N | |
| 8.9 | H | H | H | 1 | C₂H₅ | C₂H₅ | N | |
| 8.10 | H | H | H | 1 | CCl=CCl₂ | CH₃ | N | |
| 8.11 | H | H | H | 1 | Cyclopropyl | CH₃ | N | |
| 8.12 | Cl | H | H | 0 | H | CH₃ | N | m.p 195° C. (decomp.) |
| 8.13 | Cl | H | H | 0 | H | H | N | |
| 8.14 | Br | Cl | H | 0 | CH₃ | CH₃ | N | |
| 8.15 | H | H | Cl | 1 | CH₂OCH₃ | C₆H₄Cl(4) | N | |
| 8.16 | CH₃ | H | H | 0 | H | H | N | |
| 8.17 | H | CH₃ | CH₃ | 0 | CH₃ | CH₃ | N | |
| 8.18 | H | H | OCH₃ | 0 | CH₂CH=CH₂ | CH₂CH=CH₂ | N | |
| 8.19 | H | CH₃ | H | 0 | CH₂CH=CH₂ | CH₂CH=CH₂ | N | |
| 8.20 | H | H | H | 0 | H | CH₂C₆H₅ | CH | |
| 8.21 | H | H | H | 0 | H | CH₃ | N | |
| 8.22 | H | H | H | 0 | H | CH₂C₆H₅ | N | |

TABLE 9

Compounds of the formula

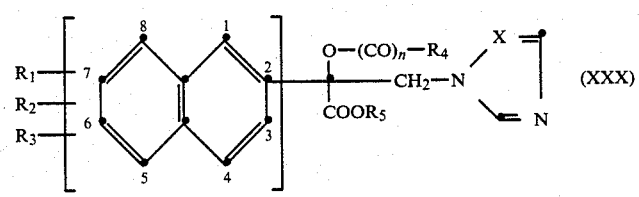
(XXX)

| Comp. No. | R₁ | R₂ | R₃ | n | R₄ | R₅ | X | Physical constants |
|---|---|---|---|---|---|---|---|---|
| 9.1 | H | H | H | 0 | H | H | N | |
| 9.2 | H | H | H | 0 | H | H | CH | |
| 9.3 | H | H | H | 0 | CH₃ | CH₃ | N | |
| 9.4 | H | H | H | 0 | CH₃ | CH₃ | CH | |
| 9.5 | H | H | H | 0 | H | CH₃ | N | m.p. 154–158° C. |
| 9.6 | H | H | H | 0 | H | CH₃ | CH | |
| 9.7 | H | H | H | 0 | H | C₂H₅ | N | m.p. 165° C. (decomp.) |
| 9.8 | H | H | H | 1 | CH₃ | CH₃ | N | |
| 9.9 | H | H | H | 1 | C₂H₅ | C₂H₅ | N | |
| 9.10 | H | H | H | 1 | CCl=CCl₂ | CH₃ | N | |
| 9.11 | H | H | H | 1 | Cyclopropyl | CH₃ | N | m.p. 181–186° C. |
| 9.12 | 6-Cl | H | H | 0 | H | CH₃ | N | |
| 9.13 | 6-Cl | H | H | 0 | H | H | N | |
| 9.14 | 6-Cl | 7-Cl | H | 0 | CH₃ | CH₃ | N | |
| 9.15 | 5-F | 7-F | H | 1 | CH₂OCH₃ | C₆H₄Cl(4) | N | |
| 9.16 | 5-CH₃ | H | H | 0 | H | H | N | |
| 9.17 | 1-CH₃ | 3-CH₃ | 4-CH₃ | 0 | CH₃ | CH₃ | N | |
| 9.18 | 5-Cl | 6-OCH₃ | H | 0 | CH₂CH=CH₂ | CH₂CH=CH₂ | N | |
| 9.19 | 6-Br | H | H | 0 | CH₂CH=CH₂ | CH₂CH=CH₂ | N | |
| 9.20 | 5-F | 7-F | H | 0 | H | CH₃ | N | |
| 9.21 | 1-OCH₃ | 6-OCH₃ | H | 0 | H | CH₃ | N | |
| 9.22 | 6-J | H | H | 1 | CCl=CCl₂ | CH₃ | N | |

TABLE 9-continued

Compounds of the formula

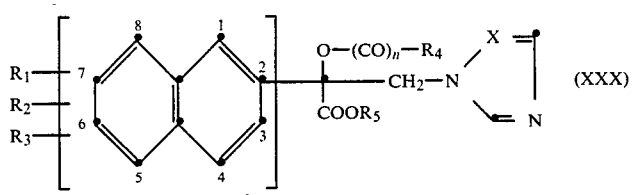

(XXX)

| Comp. No. | $R_1$ | $R_2$ | $R_3$ | n | $R_4$ | $R_5$ | X | Physical constants |
|---|---|---|---|---|---|---|---|---|
| 9.23 | H | H | H | 1 | Cyclohexyl | $CH_3$ | N | |
| 9.24 | 6-Cl | 7-Cl | H | 1 | $CCl=CCl_2$ | $CH_3$ | N | |

TABLE 10

Compounds of the formula

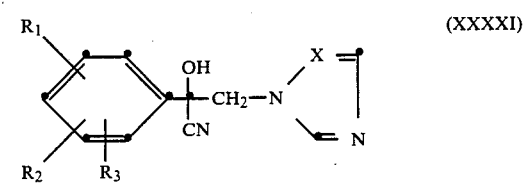

(XXXXI)

| Comp. No. | $R_1$ | $R_2$ | $R_3$ | X | Physical constants |
|---|---|---|---|---|---|
| 10.1 | 2-Cl | 4-Cl | H | N | m.p. 145° (decomp.) |
| 10.2 | 2-Cl | 4-Cl | H | CH | m.p. 136–139° C. (decomp.) |
| 10.3 | H | 4-Br | H | N | |
| 10.4 | H | H | H | N | |
| 10.5 | H | H | H | CH | |
| 10.6 | H | 4-Br | H | CH | |
| 10.7 | H | 4-Cl | H | N | |
| 10.8 | H | 4-Cl | H | CH | |
| 10.9 | 2-$CH_3$ | H | H | N | |
| 10.10 | H | 3-$NO_2$ | H | N | |
| 10.11 | H | 4-$CH_3$ | H | N | |
| 10.12 | H | 3-$CF_3$ | H | N | |
| 10.13 | 2-$CH_3$ | H | H | CH | |
| 10.14 | H | 3-$NO_2$ | H | CH | |
| 10.15 | H | 4-$CH_3$ | H | CH | |
| 10.16 | H | 3-$CF_3$ | H | CH | |
| 10.17 | 2-Cl | 4-Br | H | N | m.p. 163–170° C. (decomp.) resin |
| 10.18 | 2-Cl | 4-Br | H | CH | |
| 10.19 | 2-Cl | 3-Cl | 4-Cl | N | |
| 10.20 | 2-Cl | 3-Cl | 4-Cl | CH | |
| 10.21 | 2-Cl | H | 6-Cl | N | |
| 10.22 | 2-$CH_3$ | H | 6-$CH_3$ | N | |
| 10.23 | 2-Cl | H | 6-$CH_3$ | N | |

TABLE 11

Compounds of the formula

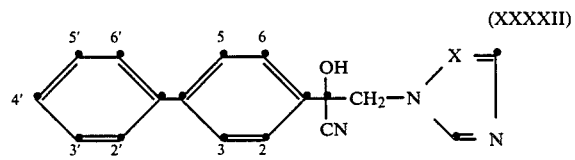

(XXXXII)

| Comp. No. | $R_1$ | $R_2$ | $R_3$ | X | Physical constants |
|---|---|---|---|---|---|
| 11.1 | H | H | H | CH | m.p. 167–174° C. |
| 11.2 | H | H | H | N | m.p. 158–166° C. (decomp.) |
| 11.3 | H | 4'-Cl | H | N | |
| 11.4 | H | 4'-Cl | H | CH | |
| 11.5 | H | 4'-Br | H | N | |
| 11.6 | 2-$OCH_3$ | H | H | N | |
| 11.7 | H | 2'-$OCH_3$ | 3'-Cl | N | |
| 11.8 | H | 4'-$CH_3$ | H | N | |
| 11.9 | H | 4'-$CH_3$ | H | CH | |

TABLE 12

Compounds of the formula

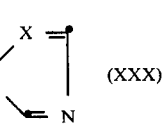

(XXXXIII)

| Comp. No. | $R_1$ | $R_2$ | $R_3$ | X | Physical constants |
|---|---|---|---|---|---|
| 12.1 | H | H | H | CH | |
| 12.2 | H | H | H | N | m.p. 169–180° C. (decomp.) |
| 12.3 | Cl | H | H | N | |
| 12.4 | Cl | H | H | CH | |
| 12.5 | Br | H | H | N | |
| 12.6 | $CH_3$ | H | H | CH | |
| 12.7 | $CH_3$ | H | H | N | |
| 12.8 | H | $CH_3$ | $CH_3$ | N | |
| 12.9 | H | H | $OCH_3$ | N | |
| 12.10 | H | $OCH_3$ | H | CH | |
| 12.11 | H | H | F | N | |

TABLE 13

Compounds of the formula (XXXXIV)

[Structure: naphthalene ring with positions labeled 3,4,5,6,7,8; substituents R₁, R₂, R₃ on the ring; side group -C(OH)(CN)-CH₂-N linked to a triazole/imidazole ring with N positions]

$$\left[ R_1, R_2, R_3 \text{ substituted naphthalene} - C(OH)(CN) - CH_2 - N \begin{array}{c} N \\ \diagdown \\ X \end{array} \right]$$

| Comp. No. | R₁ | R₂ | R₃ | X |
|---|---|---|---|---|
| 13.1 | H | H | H | CH |
| 13.2 | H | H | H | N |
| 13.3 | 6-Cl | H | H | N |
| 13.4 | 6-Cl | H | H | CH |
| 13.5 | 6-Cl | 7-Cl | H | N |
| 13.6 | 5-F | 7-F | H | N |
| 13.7 | 5-CH₃ | H | H | N |
| 13.8 | 1-CH₃ | 3-CH₃ | 4-CH₃ | N |
| 13.9 | 5-Cl | 6-OCH₃ | H | N |
| 13.10 | 5-Cl | 6-OCH₃ | H | CH |
| 13.11 | 6-Br | H | H | N |
| 13.12 | 1-OCH₃ | 6-OCH₃ | H | N |
| 13.13 | 6-J | H | H | N |

Formulation examples for active substance of the formula I (%=percent by weight)

| A. Emulsion concentrates | (a) | (b) | (c) |
|---|---|---|---|
| active substance from the Tables 1 to 13 | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenoyl-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| B. Solutions | (a) | (b) | (c) | (d) |
|---|---|---|---|---|
| active substance from the Tables 1 to 13 | 80% | 10% | 5% | 95% |
| ethylene glycol-monomethyl ether | 20% | — | — | — |
| polyethylene glycol MG 400 | — | 70% | — | — |
| N—methyl-2-pyrrolidone | — | 20% | — | — |
| epoxidised coconut oil | — | — | 1% | 5% |
| ligroin (boiling limits 160-190° C.) | — | — | 94% | — |

(MG = molecular weight)

The solutions are suitable for application in the form of very small drops.

| C. Granulates | (a) | (b) |
|---|---|---|
| active substance from the Tables 1 to 13 | 5% | 10% |
| kaolin | 94% | — |
| highly dispersed silicic acid | 1% | — |
| attapulgite | — | 90% |

The active substance is dissolved in methylene chloride, the solution is sprayed onto the carrier, and the solvent is subsequently evaporated off in vacuo.

| D. Dusts | (a) | (b) |
|---|---|---|
| active substance from the Tables 1 to 13 | 2% | 5% |
| highly dispersed silicic acid | 1% | 5% |
| talcum | 97% | — |
| kaolin | — | 90% |

Ready-for-use dusts are obtained by the intimate mixing together of the carriers with the active substance.

| E. Wettable powders | (a) | (b) | (c) |
|---|---|---|---|
| active substance from the Tables 1 to 13 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether 7-8 mols of ethylene oxide | — | 2% | — |
| highly dispersed silicic acid | 5% | 10% | 10% |
| kaolin | 62% | 27% | — |

The active substance is well mixed with the additives and the mixture is thoroughly ground in a suitable mill. There are thus obtained wettable powders which can be diluted with water to give suspensions of the required concentration.

BIOLOGICAL EXAMPLES

EXAMPLE B1

Action against *Puccinia graminis* on wheat (a) Residual protective action

Six days after being sown, wheat plants were sprayed with a spray liquor prepared from wettable powder of the active substance (0.06% of active substance). After 24 hours, the treated plants were infested with a uredospore suspension of the fungus. After an incubation time of 48 hours at about 20° C. with 95-100% relative humidity, the infested plants were kept in a greenhouse at about 22° C. An assessment of the development of rust pustules was made 12 days after infestation.

(b) Systemic action

A spray liquor prepared from wettable powder of the active substance (0.006% of active substance, relative to the volume of soil) was poured onto the soil of wheat plants 5 days after sowing. After 48 hours, the treated plants were infested with a uredospore suspension of the fungus. After an incubation time of 48 hours at about 20° C. with 95-100% relative humidity, the infested plants were kept in a greenhouse at about 22° C. An assessment of the development of rust pustules was made 12 days after infestation.

Untreated, but infested control plants exhibited a 100% rust-pustule infection, whereas plants which had been treated with compositions containing compounds of the formula I had suffered infection only slightly or not at all (<20%). Compounds of the subgroup T as well as derivatives thereof wherein n=nought and R₄=C₁-C₄-alkyl, and n=1 and R₄=C₁-C₄-alkyl, C₁-C₄-alkoxy and C₁-C₄-alkylthio (designated overall as subgroup T₂) and other compounds reduced infection to less than 10%. The compounds Nos. 1.1, 1.4-1.6, 1.8-1.14, 1.24, 1.27, 1.32, 1.40, 1.55, 1.100, 1.101, 1.116, 2.2-2.6, 2.66-2.68, 2.92, 2.109, 2.132, 2.149, 2.157 and 2.161 prevented fungus infection completely (0-5%). Compound No. 1.1 prevented fungus infection completely even at a concentration of 0.002%.

EXAMPLE B2

Action against *Cercospora arachidicola* on groundnut plants (a) Residual-protective action Groundnut plants 10-15 cm in height were sprayed with a spray liquor produced from wettable powder of the active substance (0.006% of active substance); and 48 hours later they were infested with a conidiospore suspension of the fungus. The infested plants were incubated for 72 hours at about 21° C. with high relative humidity, and were subsequently kept in a greenhouse until the typical leaf spots had appeared. The assessment of the fungicidal action was made 12 days after infestation, and was based on the number and size of the occurring spots.

(b) Systemic action

A spray liquor prepared from wettable powder of the active substance (0.06% of active substance, relative to the volume of soil) was poured onto the soil of groundnut plants 10-15 cm in height. After 48 hours, the treated plants were infested with a conidiospore suspension of the fungus, and were subsequently incubated for 72 hours at about 21° C. with high relative humidity. The plants were then kept in a greenhouse, and an assessment of the extent of fungus infection was made after 11 days.

Compared to untreated, but infested control plants (number and size of spots=100%), groundnut plants which had been treated with active substances from Tables 1 to 13 exhibited a greatly reduced level of Cercospora infection. Thus the compounds Nos. 1.1 to 1.15, 2.2-2.4, 2.66, 2.92, 2.161, 7.1-7.3, 7.23, 8.3, 8.5, 9.5 and others prevented an occurrence of spots in the above tests almost completely (0-10%).

EXAMPLE B3

Action against *Erysiphe graminis* on barley (a) Residual-protective action

Barley plants about 8 cm in height were sprayed with a spray liquor prepared from wettable powder of the active substance (0.02% of active substance). After 3-4 hours, the treated plants were dusted with conidiospores of the fungus. The infested barley plants were kept in a greenhouse at about 22° C., and the extent of fungus infection was assessed after 10 days.

(b) Systemic action

A spray liquor prepared from wettable powder of the active substance (0.006% of active substance, relative to the volume of soil) was poured onto the soil of barley plants about 8 cm in height. Care was taken to ensure that the spray liquor did not come into contact with the parts of the plants above the soil. After 48 hours, the treated plants were dusted with conidiospores of the fungus. The infested barley plants were kept in a greenhouse at about 22° C., and an assessment of the extent of fungus infection was made after 10 days.

Compounds of the formula I and compounds from the Tables 1 to 13 reduced fungus infection to below 20%, whereas untreated, but infested control plants were infected to the extnt of 100%. Compounds of the subgroups $T_2$ and T of the Example B1 reduced infection to less than 10%. A complete prevention of fungus infection (0-5%) was obtained by inter alia, the compounds Nos. 1.1-1.19, 1.24-1.27, 1.29, 1.32, 1.34, 1.40, 1.43, 1.55, 1.58, 1.109-1.111, 1.116, 2.2, 2.6, 2.66, 2.92, 2.109, 2.112, 2.132, 2.149, 2.157, 2.161, 2.181, 3.2-3.4, 4.1-4.3, 4.40, 5.2, 5.40, 5.64, 6.22, 7.23, 8.5, 9.11, 10.1 and 11.2.

EXAMPLE B4

Residual protective action against *Venturia inaequalis* on apple shoots

Apple seedlings having 10-20 cm long fresh shoots were sprayed with a spray liquor prepared from wettable powder of the active substance (0.06% of active substance). The treated plants were sprayed after 24 hours with a conidiospore suspension of the fungus. The plants were then incubated for 5 days with 90-100% relative humidity, and for a further 10 days they were kept at 20°-24° C. in a greenhouse. The extent of scab infection was assessed 15 days after infestation. Compounds Nos. 1.1 to 1.10, 1.14, 1.40, 1.55, 1.83, 1.110, 1.111, 1.116, 2.2, 2.109, 2.116 and others reduced infection to less than 10%, or in some cases prevented it completely (e.g. Compounds Nos. 1.1 and 7.3).

Shoots on apples trees cultivated outdoors are protected to the same degree, without further development of the shoots being affected.

EXAMPLE B5

Action against *Botrytis cinerea* on bean plants

Residual protective action

Bean plants about 10 cm in height were sprayed with a spray liquor prepared from wettable powder of the active substance (0.02% of active substance). The plants were infested after 48 hours with a condiospore suspension of the fungus. The extent of fungus infection was assessed after incubation of the infested plants for 3 days at 21° C. with 95-100% relative humidity. The compounds from the Tables 1 to 13 reduced in many cases fungus infection to a great extent. At a concentration of 0.02%, a fully effective action (infection 0 to 5%) was exhibited for example by the compounds Nos. 1.1, 1.6, 6.1 and 10.1.

EXAMPLE B6

Action against *Piricularia oryzae* on rice

Residual-protective action

After two weeks cultivation, rice plants were sprayed with a spray liquor prepared from a wettable powder of the active substance (0.02% of active substance). After 48 hours, the treated plants were infested with a conidiospore suspension of the fungus. Fungus infection was assessed after incubation for 5 days at 24° C. with 95-100% relative humidity.

Compared with 100% infection on unprotected plants, infection was prevented completely (0-5% infection) on plants which had been protected by the compounds Nos. 1.27 and 2.68.

What is claimed is:

1. A process for producing a mandelic acid ester of the formula Ib

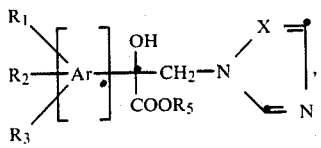
(Ib)

which process comprises reacting a corresponding α-halo-acetic acid ester of the formula IV

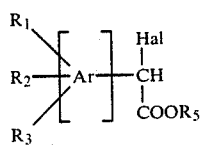
(IV)

with paraformaldehyde at 0° to 140° C. and with the desired azole of the formula VII

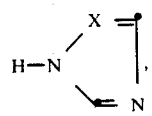
(VII)

in the presence of a base, or with the alkali salt of the azole, in an anhydrous solvent, wherein X is the bridge member —CH= or —N=,
Ar is a phenyl, diphenyl or naphthyl group,
$R_1$, $R_2$ and $R_3$ independently of one another are each hydrogen, nitro, halogen, $C_1$–$C_3$-alkyl, $C_1$–$C_3$-alkoxy or $C_1$–$C_3$-haloalkyl,
$R_5$ is hydrogen, a $C_2$–$C_{10}$-alkenyl group which is unsubstituted or substituted by halogen, a $C_2$–$C_{10}$-alkynyl group which is unsubstiuted or substituted by halogen, or it is a $C_3$–$C_8$-cycloalkyl group, or a phenyl group which is unsubstituted or substituted by halogen, $C_1$–$C_4$-alkyl, $C_1$–$C_4$-alkoxy, —CN or —$CF_3$, or it is a $C_1$–$C_{12}$-alkyl chain, which from $C_2$-alkyl and up can be interrupted by oxygen or sulfur, or is $C_1$–$C_{12}$-alkyl which is unsubstituted or substituted by a member selected from the group consisting of halogen, $C_3$–$C_8$-saturated cycloalkyl, phenyl, —COO—alkyl($C_1$–$C_4$), —CO-alkyl(-$C_1$–$C_4$), —CO-phenyl and unsaturated or saturated 5- or 6-membered ring with one hetero atom selected from the group consisting of oxygen or sulfur
and "Hal" is a halogen atom.

* * * * *